(12) United States Patent
Sugimoto et al.

(10) Patent No.: US 6,602,186 B1
(45) Date of Patent: Aug. 5, 2003

(54) ELECTRONIC ENDOSCOPE SYSTEM

(75) Inventors: Hideo Sugimoto, Tokyo (JP); Takayuki Enomoto, Saitama-ken (JP)

(73) Assignee: Pentax Corporation, Tokyo (JP)

( * ) Notice: Subject to any disclaimer, the term of this patent is extended or adjusted under 35 U.S.C. 154(b) by 56 days.

(21) Appl. No.: 09/709,708

(22) Filed: Nov. 13, 2000

(30) Foreign Application Priority Data

Nov. 11, 1999 (JP) ............................................ 11-321026
Nov. 16, 1999 (JP) ............................................ 11-325305

(51) Int. Cl.⁷ ............................................ A61B 1/045
(52) U.S. Cl. ........................ 600/126; 600/178; 600/478
(58) Field of Search ................................. 600/109, 126, 600/160, 178, 182, 476, 478

(56) References Cited

U.S. PATENT DOCUMENTS

| | | | | |
|---|---|---|---|---|
| 4,821,117 A | * | 4/1989 | Sekiguchi .............. | 600/178 X |
| 5,092,331 A | * | 3/1992 | Nakamura et al. ...... | 600/476 X |
| 5,605,531 A | * | 2/1997 | Lane et al. ............ | 600/126 X |
| 5,749,830 A | * | 5/1998 | Kaneko et al. ......... | 600/160 |
| 5,840,017 A |   | 11/1998 | Furusawa et al. ...... | 600/160 |
| 6,099,466 A |   | 8/2000 | Sano et al. ............ | 600/160 |
| 6,293,911 B1 | * | 9/2001 | Imaizumi et al. ....... | 600/160 |

* cited by examiner

Primary Examiner—Edward K. Look
Assistant Examiner—Richard A. Edgar
(74) Attorney, Agent, or Firm—Greenblum & Bernstein, P.L.C.

(57) ABSTRACT

An electronic endoscope system including a scope unit for capturing an image of an object illuminated by light using an image sensor and an image processing unit that processes the captured image to generate a video signal, is provided with a first illuminating system that illuminates the object with white light, and a second illuminating system that illuminates the object with light having a special wavelength. At least one operable switch that is operated for switching the Illumination system between the first and second systems is provided, and a switching system that switches the illuminating system between the first and second illuminating systems in response to operation of the operable switch. In such a system, the operable switch is provided at a portion accessible to an operator who is operating the scope unit.

17 Claims, 18 Drawing Sheets

ELECTRONIC ENDOSCOPE SYSTEM

BACKGROUND OF THE INVENTION

The present invention relates to an electronic endoscope system for capturing an object image using an image sensor and displaying an object image on a monitor device. More particularly, the present invention relates to an electronic endoscope system that is configured such that normal light illumination mode and a special wavelength light illumination mode can be switched.

An electronic endoscope generally includes a scope unit formed of a flexible tube, and an image signal processing unit, to which the scope unit can be detachably coupled. The scope unit is provided with an image sensor including a CCD (Charge Coupled Device) at a distal end of the flexible tube. An objective optical system is also provided at the distal end portion of the flexible tube, which forms an object image on the image sensor. Inside the scope unit, a light guide cable including optical fiber bundle is inserted. The distal end surface of the light guide cable faces an illumination lens, which is provided at the distal end of the scope unit. Further, the scope unit is formed with a treatment tool channel that allows treatment tools such as a forceps to go through. When in use, a treatment tool is inserted through the treatment tool channel, the distal end portion of the treatment tool being protruded from the distal end of the scope unit so that a desired treatment is performed.

In the image signal processing unit, a normal light source, i.e., a white light source such as a halogen lamp, xenon lamp or the like, is provided. When the scope unit is coupled to the image signal processing unit, the light emitted by the normal light source is incident on the proximal end surface of the light guide cable. When the scope unit is inserted in a cavity of a patient, the incident light proceeds in the light guide cable, and emerged through the illumination lens to illuminate an object facing the distal end of the scope unit. The light is reflected by the object, and converged by the objective optical system, which forms an optical image of the object on the light receiving surface of the image sensor. The image sensor converts the optical image to an electrical signal, which is transmitted to the image signal processor unit, where a video signal is generated and transmitted to the monitor device. Thus, the image of the object is displayed on the image screen of the monitor device.

Recently, in the field of the electronic endoscope, besides the normal light described above, light having a special wavelength is used as the illumination light for diagnosis and/or treatment.

An example of the diagnosis using light having the special wavelength is a fluorescent diagnosis using ultraviolet light as the illumination light for early detection of the cancer. It has been known that biotissues fluoresce when illuminated by the ultraviolet light, or excitation light having a predetermined wavelength. Healthy tissues emit stronger fluorescent light than the cancerous tissues. Therefore, by illuminating the tissues with the ultraviolet light (excitation light), and observing the fluorescent light emitted therefrom (i.e., a fluorescent image), the cancerous tissues can be detected at an early stage.

When the light having the special wavelength is used, an optional light guide cable for the special wavelength light becomes necessary. However, in view of the design of the scope unit, it is generally impossible to provide such an extra light guide cable inside the scope unit. Accordingly, in practice, the light guide cable for the special wavelength light is inserted in the treatment tool channel. That is, the proximal end of an extra light guide cable for the special wavelength light is coupled to a light source emitting the light having the special wavelength (e.g., an ultraviolet lamp or the like), and the extra light guide cable is inserted through the treatment tool channel. If, for example, a fluorescent image is to be observed, the excitation light is used for illuminating the object, and the fluorescent light emitted by the tissues is used for forming the optical image on the image sensor.

When the above-described diagnosis and/or treatment is carried out, it sometimes becomes necessary to switch the illuminating light between the normal light and the special wavelength light relatively frequently. In conventional electronic endoscope systems, the switching of the illumination light is carried out by an assistant operator who is different from an operator operating the scope unit. The assistant operator generally monitors operation of the entire system, and switches the illumination light following the directions of the operator. Since the directions are generally given by speech, if the illumination lights are to be switched frequently, it is very troublesome for the operator to give the directions to the assistant operator.

Further, according to another aspect, the normal light is used much more frequently than the special wavelength light. Therefore, it is preferable that the light source of the special wavelength light is turned ON/OFF appropriately. For example, if a diagnosis using the special wavelength light is to be performed after diagnosis using the normal light Is performed, it is preferable, for saving the energy and life of the light source, that the light source is turned ON immediately before it is used. Further, if the special wavelength light becomes unnecessary, the light source of the special wavelength light is preferably turned OFF immediately. Turning ON/OFF of the light source of the special wavelength light may be performed by the assistant operator. However, it is also troublesome for the operator of the scope unit to give the directions to the assistant operator, and it is preferable that turning ON/OFF of the light source of the special wavelength light Is done by the operator.

SUMMARY OF THE INVENTION

It is therefore an object of the invention to provide an improved electronic endoscope system, which uses the normal light and the light having a special wavelength as the illuminating light, and switching between the normal light and the light having the special wavelength can be done relatively easily by an operator.

Another object of the invention is to provide an electronic endoscope system, which uses the normal light and the light having a special wavelength as the illuminating light, and turning, ON/OFF a light source of the light having the special wavelength can be done easily by the operator.

According to an aspect of the invention, there is provided an electronic endoscope system including a scope unit for capturing an image of an object illuminated by light using an image sensor and an image processing unit that processes the captured image to generate a video signal, which is provided with a first illuminating system that illuminates the object with first light having a first characteristic, a second illuminating system that illuminates the object with second light having a second characteristic, at least one operable switch that is operated to instruct a switching between the first illuminating system and the second illuminating system, and a switching system that switches between the first illuminating system and the second illuminating system in response to the operation of the at least one operable switch. In this endoscope system, the at least one operable switch being provided at a portion accessible to an operator who operates the scope unit.

Since the operable switch is provided at a portion accessible to the operator who is operating the scope unit, switching between the normal light and the light having the special wavelength can be done relatively easily by the operator without asking an assistant operator to switch.

Optionally, the first illuminating system may include (a) a first light source that emits the first light, and (b) a first light guide cable inserted through the scope unit to guide the first light from the first light source to a distal end of the scope unit. Further, the second illuminating system may include (a) a second light source that emits the second light, (b) a second light guide cable inserted through the scope unit to guide the second light from the second light source to the distal end of the scope unit, and (c) a shutter provided between the second light source and the second light guide cable. With this structure, when the first illuminating system is selected, the shutter is closed so that the second light is not guided by the second light guide cable, and when the second illuminating system is selected, the shutter is opened to allow the second light to be guided by the second light guide cable and the first light source is turned OFF.

Alternatively, the first illuminating system may include (a) a first light source that emits light having a first characteristic, (b) a first light guide cable inserted through the scope unit to guide the first light from the first light source to a distal end of the scope unit, and (c) a first shutter provided between the first light source and the first light guide cable, and the second illuminating system may include (a) a second light source that emits light having a second characteristic, (b) a second light guide cable inserted through the scope unit to guide the second light from the second light source to the distal end of the scope unit, and (c) a second shutter provided between the second light source and the second light guide cable. With this construction, when the first illuminating system is selected, the second shutter is closed so that the second light is not guided by the second light guide cable, and the first shutter is opened to allow the first light to be guided by the first light guide cable, and when the second illuminating system is selected, the first shutter is closed so that the first light is not guided by the first light guide cable, and the second shutter is opened to allow the second light to be guided by the second light guide cable.

Further optionally, the first illuminating system may include a first light source that emits light having a first characteristic, the second illuminating system may include a second light source that emits light having a second characteristic, and the electronic endoscope may further include a controlling system that controls the second light source to turn ON and OFF. With this construction, if the second light source is turned OFF and the at least one operable switch is operated in a predetermined manner, the second light source is turned ON, and if the second light source is turned ON and the at least one operable switch is operated in the predetermined manner, the second light source is turned OFF.

According to another aspect of the invention, there is provided an electronic endoscope system including a scope unit for capturing an image of an object illuminated by light using an image sensor and an image processing unit that processes the captured image to generate a video signal. The electronic endoscope may further include a first illuminating system that illuminates the object with white light, a second illuminating system that illuminates the object with light having a special wavelength, at least one operable switch that is operated to instruct a switching between the first illuminating system and the second illuminating system;

a switching system that switches between the first illuminating system and the second illuminating system in response to the operation of the at least one operable switch, the at least one operable switch being provided at a portion accessible to an operator who operates the scope unit.

Optionally, at least one operable switch may include a foot switch which can be operated by a foot of the operator.

Further optionally, the scope unit may be provided with an instrument channel through which a treatment tool can be inserted, the at least one operable switch including a manually operable switch arranged adjacent to an inlet of the instrument channel.

Furthermore, the scope unit may have an operation section, at which operation switches are provided, and at least one operable switch may include another manually operable switch arranged at the operation section.

Still optionally, the first illuminating system may include (a) a white light source that emits white light, and (b) a light guide cable inserted through the scope unit to guide the white light from the white light source to a distal end of the scope unit, and the second illuminating system may include (a) a special wavelength light source that emits light having a special wavelength, (b) another light guide cable inserted through the instrument channel to guide the light having the special wavelength from the special wavelength light source to the distal end of the scope unit, and (c) a shutter provided between the special wavelength light source and the another light guide cable. With this construction, when the first illuminating system is selected using the at least one operable switch for illuminating the object, the shutter is closed so that the special wavelength light is not guided by the another light guide cable, and when the second illuminating system is selected using the at least one operable switch for illuminating the object, the shutter is opened to allow light having the special wavelength to be guided by the another light guide cable and the white light source is turned OFF.

Alternatively, the first illuminating system may include (a) a white light source that emits white light, (b) a first light guide cable inserted through the scope unit to guide the white light from the white light source to a distal end of the scope unit, and (c) a first shutter provided between the white light source and the light guide cable, and the second illuminating system may include (a) a special wavelength light source that emits light having a special wavelength, (b) a second light guide cable inserted through the instrument channel to guide the light having the special wavelength from the special wavelength light source to the distal end of the scope unit, and (c).a second shutter provided between the special wavelength light source and the second light guide cable. With this construction, when the first illuminating system is selected using the at least one operable switch for illuminating the object, the second shutter is closed so that the special wavelength light is not guided by the second light guide cable, and the first shutter is opened to allow the white light to be guided by the first light guide cable, and when the second illuminating system is selected using the at least one operable switch for illuminating the object, the first shutter is closed so that the white light is not guided by the first light guide cable, and the second shutter is opened to allow the light having the special wavelength to be guided by the second light guide cable.

Further optionally, a performance of the image processing unit is changed in accordance with the operation of the at least one operable switch so that an appropriate image processing operation is performed depending on a selected one of the first and second illuminating systems. In this case, the image processing unit may include an amplifier that amplifies image signals output by the image sensor, a gain of the amplifier when the second illuminating system is selected being higher than a gain when the first illuminating system is selected.

Optionally, the light having the special wavelength is UV light.

In a particular case, the first illuminating system may include a white light source that emits white light, the second illuminating system may include a second light source that emits light having a special wavelength, and the electronic endoscope may further include a controlling system that controls the second light source to turn ON and OFF. With this construction, if the second light source is turned OFF and the at least one operable switch is held operated for a predetermined duration of time, the second light source is turned ON, and if the second light source is turned ON and the at least one operable switch is held operated for a predetermined duration of time, the second light source is turned OFF. Further, in this case, at least one operable switch including a foot switch which can be operated by a foot of the operator.

Still optionally, the scope unit may be provided with an instrument channel through which a treatment tool can be inserted, and at least one operable switch may include a manually operable switch arranged adjacent to an inlet of the instrument channel.

Further optionally, the scope unit may have an operation section, at which operation switches are provided, and at least one operable switch may include another manually operable switch arranged at the operation section.

BRIEF DESCRIPTION OF THE ACCOMPANYING DRAWINGS

DESCRIPTION OF THE EMBODIMENTS

Hereinafter, refereeing to the accompanying drawings, embodiments according to the present invention will be described.

First Embodiment

Figure 1:
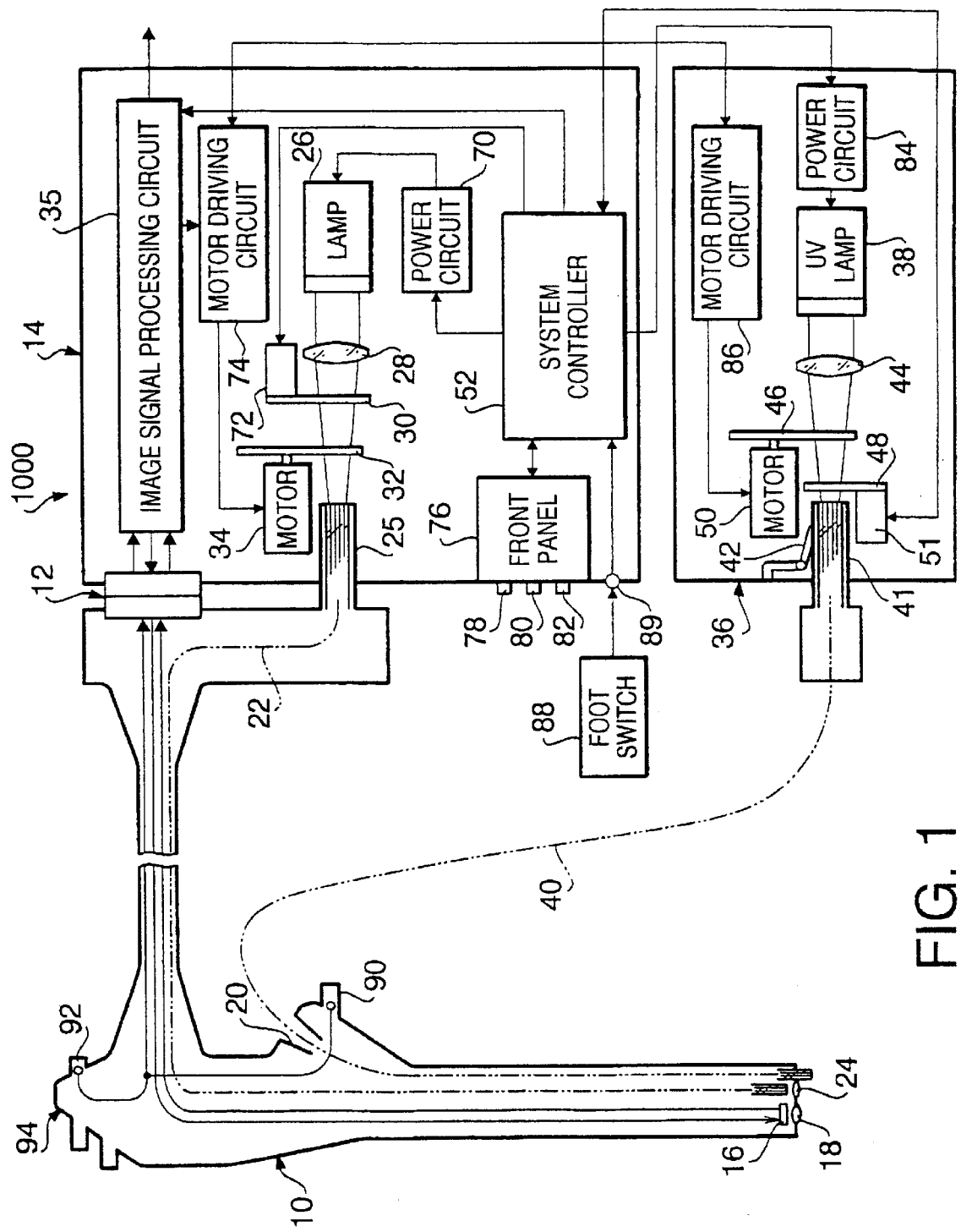
FIG. 1 is a block diagram of an electronic endoscope system according to an embodiment of the invention.

FIG. 1 is a block diagram of an electronic endoscope system 1000 according to a first embodiment of the invention. The electronic endoscope system 1000 includes a scope unit 10 including a flexible tube, and an image signal processing unit 14. The proximal end of the scope unit 10 is connected to the image signal processing unit 14 through a connector 12. At the distal end of the scope unit 10, an image sensor including a solid state image capturing element is provided. In the present embodiment, a CCD (charge coupled device) 16 serves as the image capturing element. The image sensor is also provided with an objective lens system 18 which forms an image of an object on an image receiving surface of the CCD 16. The scope unit 10 is formed with a treatment tool channel 20. A treatment tool such as a forceps is to be inserted through the treatment tool channel 20. When in use, the distal end of the inserted treatment tool is protruded from the distal end surface of the scope unit 10.

A light guide cable 22, which is formed of a bundle of optical fibers and transmits white light (i.e., normal light), is inserted through the scope 10. A distal end of the light guide cable 22 is located at the distal end of the scope unit 10. On a distal end surface of the scope unit 10, an illumination lens 24, from which light for illuminating an object, is provided to face the distal end surface of the light guide cable 22. At a proximal end portion of the light guide cable 22, an appropriate connection adaptor 25, which connects the light guide cable 22 with a white light source 26 such as a xenon lamp, halogen lamp or the like is provided. The white light source 26 is incorporated in the image signal processing unit 14. In FIG. 1, a part of the light guide cable 22 is indicated by two-dotted lines. As shown in FIG. 1, inside the image signal processing unit 14, a collecting lens 28 and an aperture unit 30 are arranged, in this order, between the connector 25 and the white light source 26. The collecting lens 28 converges the white light emitted by the white light source 26 on a proximal end surface of the light guide cable 22. The aperture unit 30 is controlled to change the aperture size so that the amount of light incident on the proximal end surface of the light guide cable 22 is adjusted.

Figure 2:
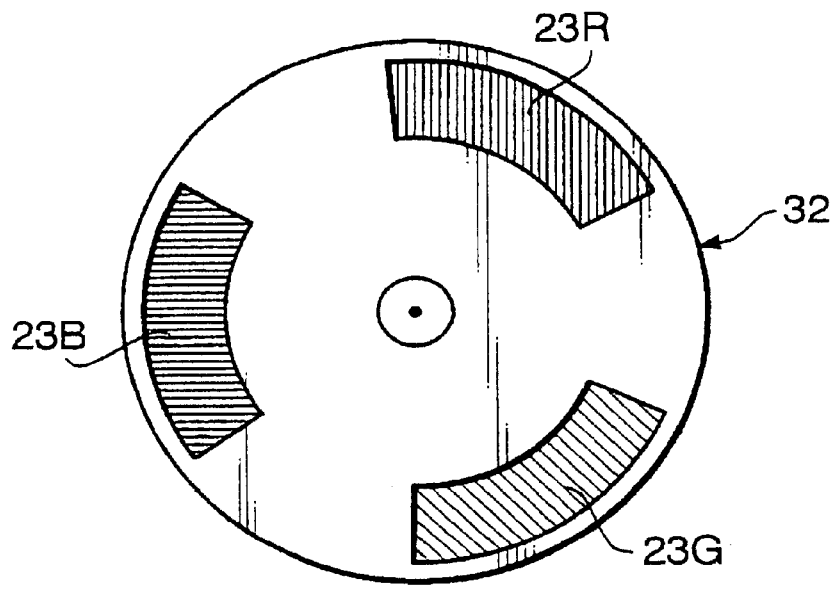
FIG. 2 is a front view of a rotary color filter provided in an image signal processing unit of the endoscope system shown in FIG. 1.

In the electronic endoscope system 1000 shown in FIG. 1, a so-called surface sequential method is employed to obtain a color image. That is, red, green and blue image components are captured separately, and they based on the color components, a color video signal is generated. For this purpose, a rotary color filter 32, which includes a three primary color filters, is provided between the proximal end surface of the light guide cable 22 and the aperture unit 30. As shown in FIG. 2, the rotary RGB filter 32 includes a disc member having a red filter element 32R, a green filter element 32G and a blue filter element 32B. Each of the color filter elements 32R, 32G and 32B is formed to be sector-shaped. The color filter elements 32R, 32G and 32B are arranged at peripheral portion, along the circumference thereof, the filter elements 32R, 32G and 32B being angularly spaced from each other by 120° with respect to the center of the disk. Portions between the adjoining filter elements are formed to be light shielding areas.

Figure 3:
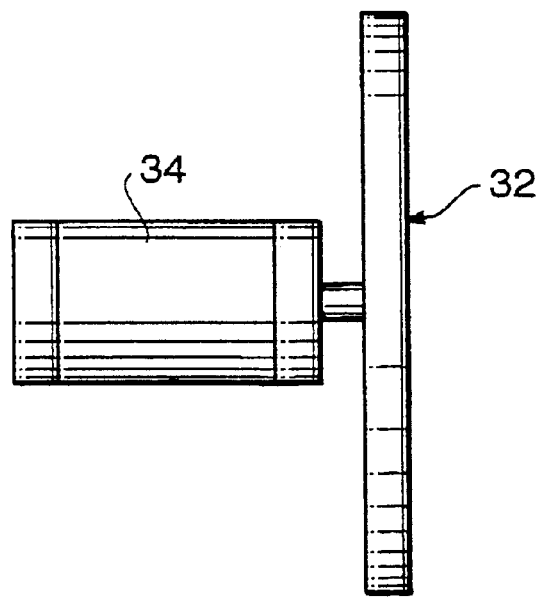
FIG. 3 is a side view of the rotary color filter shown in FIG. 2.

As best shown in FIG. 3, the color filter 32 is rotated by a motor 34 such as a servo motor or a stepping motor. The frequency of rotation of the rotary filter 32 is determined in accordance with a TV standard employed in the endoscope system 1000. For example, if the NTSC standard is employed, the rotary filter 32 is rotated generally at 30 rps (revolution per second). If the PAL standard is employed, the rotary filter 32 is rotated generally at 25 rps.

If the color filter 32 rotates at 30 rps (i.e., NTSC standard), a period for one revolution is approximately 33.3. ms (i.e., 1/30 sec.). Therefore, a period within which the object is illuminated by the light passed through each filter element (32R, 32G and 32B) is approximately 33/6 ms. From the distal end surface of the light guide cable 22, red light, green light and blue light are emerged sequentially for approximately 33/6 ms each at every 33.3 ms (1/30 sec.). Accordingly, the object is illuminated with red, green and blue light sequentially, and an image of each color component is formed on the light receiving surface of the CCD 16 by the objective lens 18 sequentially. The CCD 16 photo-converts each of the color component images into analog pixel signals for one image frame. The analog pixel signals are output by the CCD 16 in the light shielding period of 33/6 ms following the illumination period of 33/6 ms. The analog pixel signals for one image frame is then transmitted to the image signal processing circuit 35 in the image signal processing unit 14. Thus obtained pixel signals of the red, green and blue components are processed at the image signal processing unit 14, which outputs a color video signal to a TV monitor device (not shown), where a color object image is displayed.

In the present embodiment, the electronic endoscope system 1000 is further.provided with a special wavelength light source unit 36, which includes a UV (ultra-violet) lamp 38. The special wavelength light source unit 36 is detachably coupled with a proximal end of a light guide cable 40 for transmitting the special wavelength light (the UV light in this embodiment). That is, at the proximal end of the light guide cable 40, a suitable adapter 41 is provided. By inserting the adapter 41 through a connection opening (not numbered) formed on a wall of the housing of the special wavelength light source unit 36, the proximal end of the light guide cable 40 is optically connected with the UV lamp 38. It should be noted that, in FIG. 1, 42 denotes an openable cover 42 provided at the connection opening. The cover 42 is urged to neutrally close the connection opening, and can be displaced at an open position as shown in FIG. 1 when the adapter 41 is inserted in the connection opening.

At the distal end portion of the light guide cable 40, an illumination lens system may be provided, if necessary. The distal end of the light guide 40 is inserted in the instrument tool channel 20 of the scope unit 10 as shown in FIG. 1. When the distal end of the light guide cable 40 has reached the tip end of the instrument tool channel 20, a front portion of the distal end of the scope unit 10 is illuminated with the UV light. The light guide cable 40 can be protruded from and retracted inside the instrument tool channel 20 similarly to the instrument tools such as a forceps. Thus, by moving the light guide cable 40 along the instrument tool channel 20, the intensity of UV light illuminating the object can be adjusted. In FIG. 1, as in the light guide cable 22, a part of the light guide cable 40 is indicated by two-dotted lines to simplify the drawing.

As is apparent from FIG. 1, in the special wavelength light source unit 36, a collecting lens 44 is arranged between the proximal end of the light guide cable 40 and the UV lamp 38. The light collecting lens 44 converges the UV light emitted by the UV lamp 38 on a proximal end surface of the light guide cable 40. Between the proximal end surface of the light guide cable 40 and the collecting lens 44, a rotary shutter 46 and a shutter 48 are provided.

The rotary shutter 46 is similar to the rotary filter 32 except that the color filter elements 32R, 32G and 32B are replaced with openings. The rotation speed of the rotary shutter 46 is also determined in accordance with the TV standard employed in the endoscope system. For example, 30 rps for NTSC standard, and 25 rps for PAL standard. In FIG. 1, 50 denotes a motor such as a servo motor or a stepping motor for rotating the rotary shutter 46.

If the rotary shutter 46 rotates at 30 rps (i.e., NTSC standard), a period for one rotation is approximately 33.3 ms (i.e., 1/30 sec.). Therefore, a period within which the object is illuminated by the UV light passed through each opening is approxlmately 33/6 ms. From the distal end surface of the light guide cable 40, the UV light is emerged for approximately 33/6 ms at every 33/6 ms. Accordingly, the object is illuminated with the UV light for 33/6 ms at every 33/6 ms.

When the UV light is incident, the object (biotissues) fluoresces, and an image of the fluorescing tissues is formed on the light receiving surface of the CCD by the objective lens 18. It should be noted that the UV light reflected by the object is also converged on the light receiving surface of the CCD 16. To remove the UV light component,an optical filter, which shields the UV light component and allows the fluorescent light component as well as visible light components including the red, green and blue components to pass through, is provided in front of the light receiving surface of the CCD 16. The CCD 16 photo-converts the image (i.e., a fluorescent light image) into analog pixel signals for one image frame. The analog pixel signals are output by the image sensor 16 during the light shielding period 33/6 ms following the illumination period 33/6 ms. The analog pixel signals for one frame are then transmitted to the image signal processing circuit 35 in the image signal processing unit 14. Thus obtained pixel signals of the fluorescent tissues are processed at the image signal processing unit 14, and are output as a monochromatic video signal to a TV monitor device (not shown), where a fluorescent image of the object is displayed.

The shutter 48 is driven to open/close by an actuator 51, which is controlled by the system controller 52. The shutter 48 prevents., when closed, the UV light from impinging on the proximal end surface of the light guide cable 40. When a color image is captured using the white light source 26, the shutter 48 is closed. The shutter 48 is opened only when the fluorescent image is to be captured. It should be noted that when the fluorescent image is to be captured, the white light source 26 is turned OFF.

In summary, according to the first embodiment, when the object is to be illuminated with the UV light and the fluorescent image is to be captured, the UV lamp 38 is tuned ON, and the UV light is prevented from impinging on the proximal end surface of the light guide by closing the shutter 48. When the UV light is incident on the light guide cable 40 and the fluorescent image is being captured, the white light source 26 is turned OFF.

As shown in FIG. 1, the image signal processing unit 14 Is provided with the system controller 52, which is composed of, for example, a microprocessor. The system controller 52 includes a CPU (Central Processing Unit), a ROM containing programs to be executed and coefficients referred to during operation, a RAM for temporarily storing data and the like, and I/O interfaces. Since such devices are well-known, they are not shown in the drawings. The entire operation.of the endoscope system is controlled by the CPU of the system controller 52.

Figure 4:
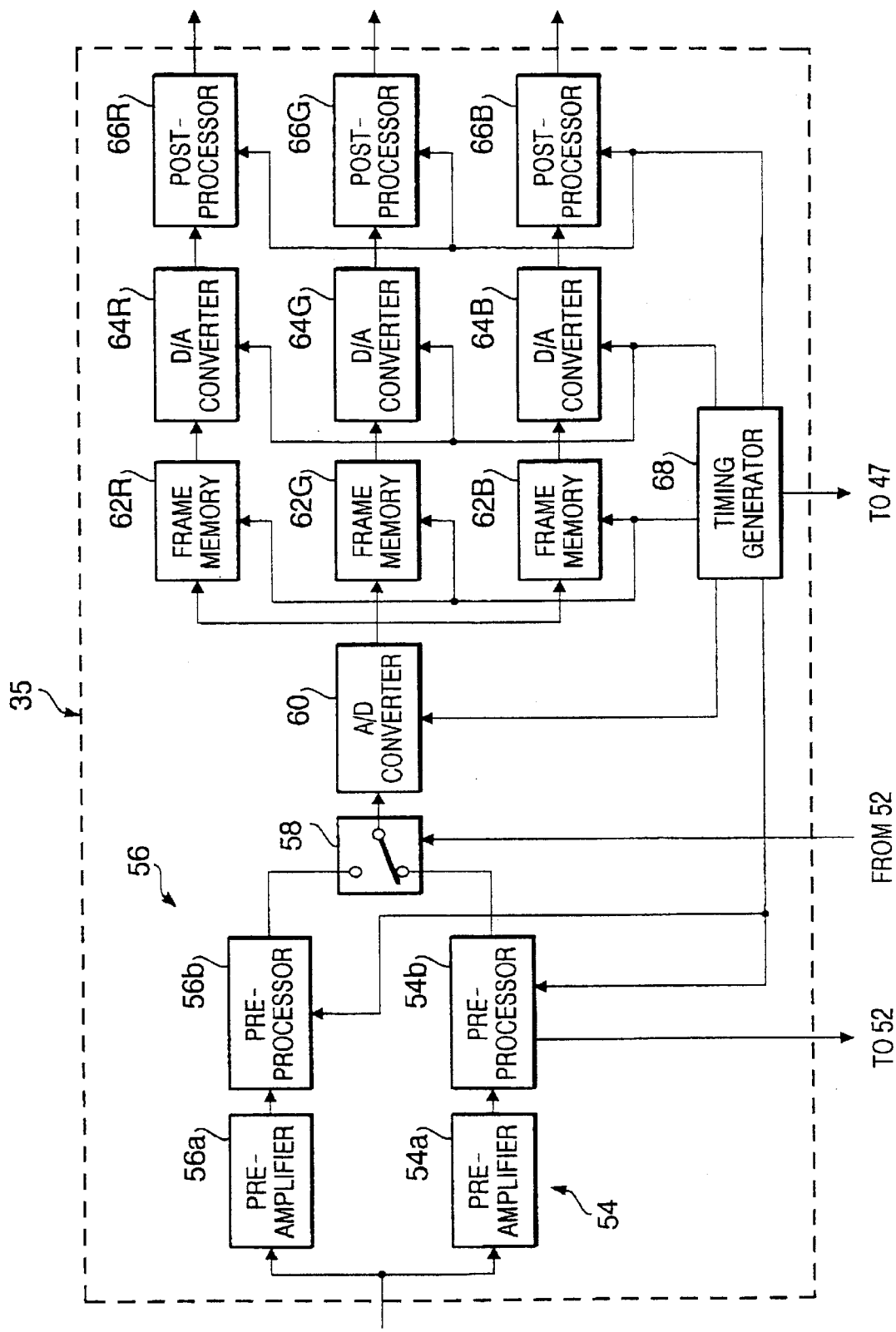
FIG. 4 is a block diagram of an image signal processing unit according to a first embodiment of the invention, which can be employed in the electronic endoscope system shown in FIG. 1.

FIG. 4 shows an example of a configuration of the image signal processing circuit 35. In this example, the image signal processing circuit 35 includes first and second signal input systems 54 and 56, which are arranged in parallel with each other. The first input system 54 includes a serially connected pre-amplifier 54a and a pre-processor. 54b. The second input system 56 includes a serially connected pre-amplifier 56a and a pre-processor 56b. A switching circuit 58 and an A/D converter 60 are provided in the image signal processing circuit 35. Outputs of the first and second input systems 54 and 56 (i.e., output ports 54b and 56b of the pre-processors 54b and 56b) are selectively connected with the input port of the A/D converter 60 via the switching circuit 58.

Regardless whether the three primary color illuminations or the UV light illumination is performed, the pixel signals output by the CCD 16 are input to either of the first and second input systems 54 and 56. Depending on whether the three primary color images are to be captured (this operation mode of the endoscope system 1000 will be referred to as a color image mode hereinafter) or the fluorescent image is captured (this operation mode will be referred to as a fluorescent image mode), the switching circuit 58 is switched. If the primary color images are being captured, the switching circuit 58 is controlled to connect the first input system 54 to the input port of the A/D converter 60. If the fluorescent image is being captured (i.e., when the endoscope system 1000 operates in the fluorescent image mode), the switching circuit 58 is controlled to connect the second input system 56 to the A/D converter 60. The first input system 54 is for processing the pixel signals of each of the three primary color images, and the second input system 56 is for processing the monochromatic pixel signals. The switching operation of the switching circuit 58 is set by a control signal transmitted by the system controller 52.

The pixel signals for the three primary color components subsequently transmitted from the CCD 16 when the endoscope system 1000 operates in the color image mode is amplified by the pre-amplifier 54a that has a predetermined gain, and then, by the pre-processor 54b, predetermined image processing operations such as filtering, white balance compensation, gamma compensation, outline enhancement, clamp processing and the like are performed. The processed analog pixel signals for one image frame is converted into digital pixel signals by the A/D converter 60, and stored in one of the frame memories 62R, 62G and 62B. That is, the red digital pixel signals for one frame are stored in the frame memory 62R, the green digital pixel signals for the frame are stored in the frame memory 62G and the blue digital pixel signals for the same frame are stored in the frame memory 62B as color image signals.

Next, the digital image signals for the three primary colors (i.e., the red digital image signal, the green digital image signal and the blue digital image signal) are read out of the frame memories 62R 62G and 62B, respectively. Then, to each of the digital image signals, a horizontal synchronizing signal and a vertical synchronizing signal are added. The digital image signals for one image frame includes the red, green and blue digital image signals, which are read out of the frame memories 62R, 62G and 62B, respectively, and output therefrom as color digital video signals for one frame. Then, the red digital video signal, the green digital video signal, and the blue digital video signal are converted into red, green and blue analog video signals by D/A converters 64R, 64G and 64B, respectively. The converted red, green and blue analog video signals are input to post-processor 66R, 66G and 66B for red, green and blue components, respectively, and then output to, the monitor device.

In the post-processors 66R, 66G and 66B predetermined image processing operations, such as filtering, color balancing, gamma correction, outline enhancement and the like are applied to the respective analog video signals. The red, green and blue analog video signals as processed are output from the image signal processing circuit 35 as color video signals to the monitor device. Then, a color image of the object captured by the CCD 16 is displayed on the monitor device.

As shown in FIG. 4, the image signal processing circuit 35 includes a timing generator 68, which outputs clock pulses having predetermined frequencies to the pre-processors 54b and 56b, A/D converter 60, frame memories 62R, 62G and 62B, D/A converters 64R, 64G and 64B, and post-processors 66R, 66G and 66B, respectively. Operations and/or signal processing are performed in accordance with the clock signals input to each of the above elements. That is:

- various image processing operations in the pre-processor 54b are performed synchronously with the clock signal input therein;
- sampling of pixel signals at the A/D converter 60 is performed synchronously with the clock signal input therein;
- reading/writing the image signals from/in the frame memories 62R, 62G and 62B is performed synchronously with reading/writing clock signals, respectively;
- sampling of the analog video signal at the D/A converters 64R, 64G and 64B is performed synchronously with the clock signal input therein; and
- image processing operations in the post-processors 66R, 66G and 66B are performed synchronously with the clock signals input therein.

The pixel signals for one frame of the fluorescent image subsequently transmitted from the CCD 16 is amplified by the pre-amplifier 56a that has a predetermined gain, and then, by the pre-processor 56b, predetermined processing operations such as filtering, gamma correction, outline enhancement, clamp processing and the like are applied. The processed monochromatic (fluorescent) analog pixel signals for one image frame are converted into digital pixel signals by the A/D converter 60, and stored in one of the frame memories 62R, 62G and 62B as digital image signals.

The CCD 16 has a lower sensitivity for light having smaller wavelength than for light having longer wavelength. Accordingly, the CCD 16 has a relatively low sensitivity for the fluorescent light. Therefore, the gain of the pre-amplifier 56a is greater than that of the pre-amplifier 54a. Due to this configuration, however, noise level of the monochromatic analog pixel signals becomes relatively high. Therefore, in the pre-processor 56b, noise-removing band width is set corresponding to the characteristic of the pre-amplifier 56a. That is, setting of noise removing characteristics of the pre-processor 56b is different from that of the pre-processor 54b.

Further, since the sensitivity of the CCD 16 for the visible light is different from that for the fluorescent light, characteristics for the clamp processing, i.e., processing for determining a pedestal level of the analog pixel signals of the pre-processor 56b are different from those of the pre-processor 54b.

As above, the pre-amplifier 54a and the pre-processor 54b of the first input system are configured to suitably process the analog pixel signals when the object is sequentially illuminated with three primary color light, and the pre-amplifier 56a and the pre-processor 56b of the second input system are configured to suitably process the monochromatic analog pixel signals when the UV light is used for illuminating the object.

Next, the digital image signals for the monochromatic digital image are read out from the frame memories 62R, 62G and 62B, simultaneously. Then, to each of the digital Image signals, the horizontal synchronizing signal and vertical synchronizing signal are added. Specifically, digital image signals for one image frame are read out of the frame memories 62R, 62G and 62B, simultaneously, which are output as monochromatic digital video signals for one frame. Then, the each digital video signal, is converted into analog video signals by D/A converters 64R, 64G and 64B. The converted analog video signals are input to post-processor 66R, 66G and 66B.

In the post-processors 66R, 66G and 66B, predetermined image processing operations, such as filtering, gamma correction, outline enhancement and the like are applied to the respective analog video signals.

As described above, the rotary shutter 46 is constructed such that the filter elements of the rotary filter 32 are replaced with openings. Therefore, when the UV light is used for illuminating the object, three frames of monochromatic analog video signals can be obtained for one rotation of the rotary shutter 46. The three frames of monochromatic analog pixel signals are converted into monochromatic digital pixel signals for three frames by the A/D converter 60, and stored in the frame memories 62R, 62G and 62B, respectively. Thus, the monochromatic analog signal can be obtained without making a substantial change in the image signal processing circuit 35. It should be noted that, in the endoscope system 1000, only one of the three monochromatic video signals is used for display the fluorescent image on the monitor device.

Although a connection between the CCD 16 and the timing generator 68 is not shown in FIG. 1, they are connected, and the operation of the CCD 16 (i.e., capturing of an image) is performed in accordance with a clock signal, which has a predetermined frequency, output by the timing generator 68.

As shown in FIG. 1, the image signal processing unit 14 is provided with a power circuit 70, which supplies electricity to the white light source 26 under control of the system controller 52. The power circuit 70 is connected to a commercial power source through a not shown connection plug.

Further, as shown in FIG. 1, the aperture unit 30 is provided with an actuator 72 that changes the aperture size under control of the system controller 52.

Specifically, in the pre-processor 54b of the first input system 54, an integration circuit is implemented. Through the integration circuit, a brightness evaluation signal, which is used for evaluating the analog pixel signals for three primary colors obtained at every one revolution of the color filter 32, is obtained. The brightness evaluation signal is converted into digital brightness evaluation data and input to the system controller 52. Then, the system controller 52 controls the actuator 72 to change the aperture size of the aperture unit 30 so that the brightness evaluation data value coincides with a predetermined reference brightness data value. With the above control of the aperture unit 30, regardless of the distance of the object with respect to the distal end of the scope unit 10, the brightness of the color image displayed on the monitor device is maintained substantially constant.

Furthermore, as shown in FIG. 1, the image signal processing unit 14 is provided with a motor drive circuit 74, which drives the motor 34 for rotating the color filter 32. The motor 34 is driven in accordance with driving pulses output by the motor driving circuit 74. As aforementioned, the rotation speed of the motor 34, i.e., the rotation speed of the color filter 32, is determined based on the TV standard as employed (e.g., 30 rps for NTSC standard; 25 rps for PAL standard). Of course, rotation of the color filter 32 should be performed synchronously with the signal processing operations performed in the image signal processing circuit 35. For this purpose, timing of the drive pulses is controlled in accordance with the clock pulse output by the timing generator 68.

A front panel 76 is provided on the outer surface of the housing of the image signal processing unit 14. Various switches, indicators and lamps are provided at the front panel 76. In particular, a mode switch 78, a white light power switch 80, and a power switch 82 of the image signal processing device 14 are provided at the front panel 76.

As shown in FIG. 1, a power circuit 84 that supplies electricity to the UV lamp 38 is provided in the special wavelength light source unit 36. The power circuit 84 is connected to the commercial power source through a connection plug (not shown). The power circuit 84 is connected with the system controller 52 through a cable, and supply of the electricity from the lamp power circuit 84 to the UV lamp 38 is controlled by the system controller 52. In the first embodiment, the UV lamp 38 is turned ON when the white light power switch 80 is operated to turn ON the white light source 26. Optionally, the UV lamp is turned ON/OFF by operating a switch (not shown) provided to the special wavelength light source unit 36.

Further, as shown in FIG. 1, the special wavelength light source unit 36 is provided with a motor driving circuit 86 that drives the motor 50 to rotate the rotary shutter. The motor 50 is driven In accordance with driving pulses output by the motor driving circuit 86. The rotation speed of the rotation of the motor 50, i.e., the speed of the revolution of the rotary shutter 46 is determined in accordance with the employed TV standard (e.g., 30 rps for NTSC standard; and 25 rps for PAL standard). Similarly to the control of the color filter 32, the rotation of the rotary shutter 46 should be controlled synchronously with image processing operation in the image signal processing circuit 35. Therefore, the motor driving circuit 86 is connected to the motor driving circuit 74 of the image signal processing unit 14 through a cable. The timing of the driving pulses from the motor driving circuit 86 to the motor 50 is controlled in accordance with a predetermined clock pulse output by the timing generator 52.

As described above, the mode switch 78 for switching the operation mode of the endoscope system 1000 between the normal image mode and the fluorescent image mode is provided at the front panel 76. In the first embodiment, three more mode switches having the same function are provided, which can easily be operated by an operator handling the scope unit 10 when necessary. The mode switches will be described in detail below.

First one of the additional mode switches is provided as a foot switch 88 (see FIG. 1) which can be operated by foot of the operator. The foot switch 88 is placed on the floor where the electronic endoscope system 1000 is located. The foot switch 88 is connected with the system controller 52 via a detachable connector 89. The color image mode and the fluorescent image mode (i.e., three primary color illumination and the UV illumination) alternate upon operation of the foot switch 88.

Second one of the mode switches is a manually operable mode switch 90, provided to the scope unit 10 at a position adjacent to the inlet of the treatment instrument insertion channel 20. The mode switch 90 is connected to the system controller 52 through the connector 12. The color image mode and the fluorescent image mode alternate upon operation of the mode switch 90.

Third one of the mode switches is a manually operable mode switch 92, which is provided to the operation section 94 of the scope unit 10. The mode switch 92 is also connected to the system controller 52 through the connector 12, and upon operation of the mode switch 92, the three primary color illumination and the UV illumination are alternated. It should be noted that an operation knob and various switches to be operated by the operator of the scope unit 10 are provided at the operation section 94, and therefore, it is advantageous to provide the mode switch at the operation section 94.

Figure 5:
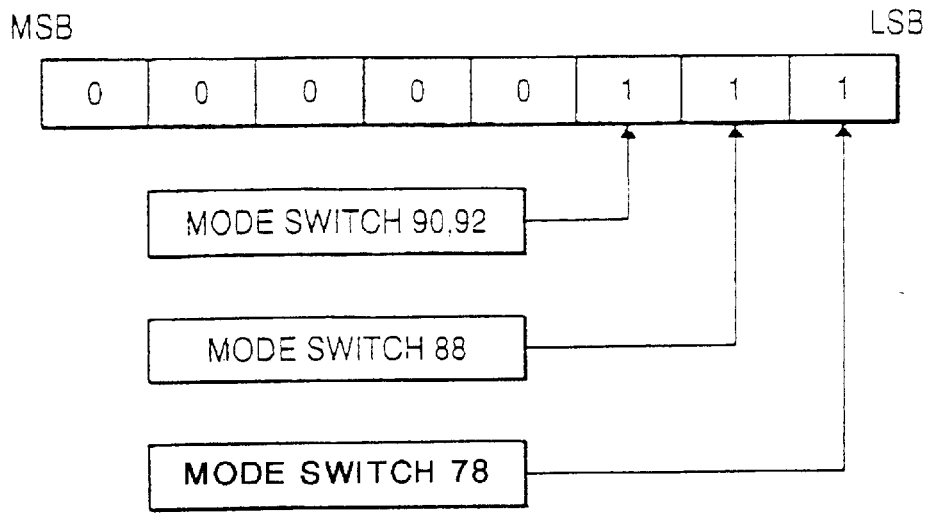
FIG. 5 shows a relationship between an input port of the image signal processing unit shown in FIG. 3 and illumination switches.

According to the first embodiment, the I/O interface of the system controller is configured to have an eight-bit input port for the four mode switches 78, 88, 90 and 92, as shown in FIG. 5, which is a conceptual structure of the input port. The LSB (least significant bit) is assigned to the mode switch 78, the second bit is assigned to the foot switch 88, and the third bit is assigned to the mode switches 90 and 92. It should be noted that the mode switches 90 and 92 are connected to the same signal line as shown in FIG. 1, and the signal line is connected to the third bit of the input port through the connector 12.

When the power switch 82 is turned ON, a predetermined high voltage,(e.g., 5 volts) is applied to signal lines of the mode switches 78 and 88, and the signal line of the mode switches 90 and 92. Then, in each of the lower three bits of the input port, a high level signal is input, and the lower three digits are set to one (1), while the other five bits are set to zero (0), as shown in FIG. 5.

Each of the mode switches 78, 88, 90 and 92 are constructed such that it is neutrally opened, and grounded when being operated. Therefore, when one of the mode switches 78, 88, 90 and 92 is operated, the corresponding bit of the input port is set to zero (0). Thus, by detecting the value of each bit, operation status of the mode switches 78, 88, 90 and 92 can be detected.

Specifically, the CPU of the system controller 52 detects the status of the input port as hexadecimal number at every predetermined interval, for example 50 ms. If none of the switches 78, 88, 90 and 92 are operated, 07h (i.e., $[00000111]_2$) is detected. If the mode switch 78 is operated, 06h (i.e., $[00000110]_2$) is detected. If the mode (foot) switch 88 is operated, 05h (i.e., $[00000101]_2$) is detected. If the mode switch 90 or 92 is operated, 03h (i.e., $[00000011]_2$) is detected. If the hexadecimal number is not 07h, it is determined that one of the switches 78, 88, 90 or 92 is operated.

Figure 6:
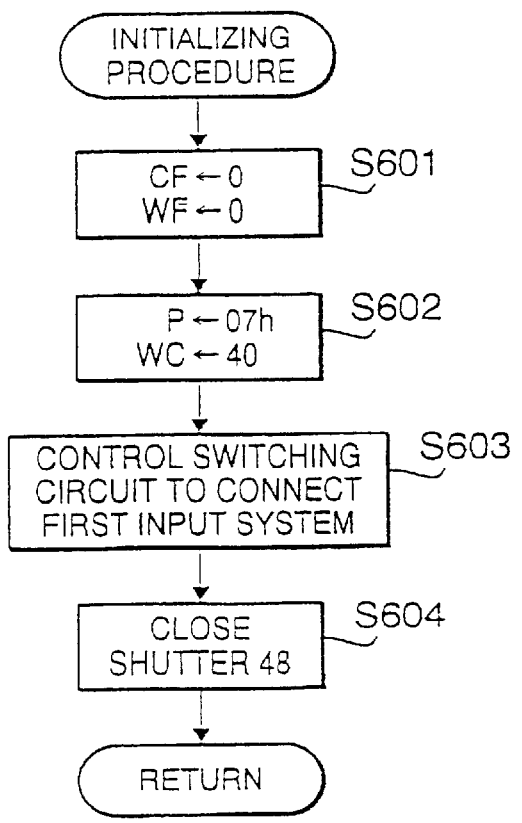
FIG. 6 is a flowchart of an initializing procedure according to a first embodiment of the invention.

FIG. 6 is a flowchart illustrating an initial setting procedure executed by the CPU of the system controller 52. The procedure shown in FIG. 6 is executed when the power switch 82 is turned ON.

At S601, flags CF and WF are initialized (i.e., set to zero (0)). The flag CF represents currently selected operation mode (i.e., currently selected illuminating light source). When CF is set to zero (0), the color image mode is selected, and when CF is set to one (1), the fluorescent image mode is selected. When the power switch 82 is turned ON, the color image mode is selected as a default mode. The flag WF is referred to when a mode change procedure, which will be described later, is executed. Every time when the operation mode is alternated, the flag WF is changed from zero (0) to one (1), and then for a predetermined interval (e.g., two seconds) therefrom, the operation of the mode switches 78, 88, 90 and 92 is not accepted.

At S602, a variable p is set to 07h as an initial value, and a counter WC is set to forty (40) as an initial value. The variable p and the counter WC are referred to in the mode change procedure shown in FIG. 7.

At S603, the switching circuit 58 is set to connect the first input system 54 to the A/D converter 60, then, at S604, the shutter 48 is driven to close. It should be noted that the procedures at S603 and S604 correspond to the procedure at S601, where the color image mode is selected. If the fluorescent image mode is a default mode, the switching circuit 58 is set to connect the second input system 56 to the A/D converter 60, and the shutter 48 is opened.

Figure 7:
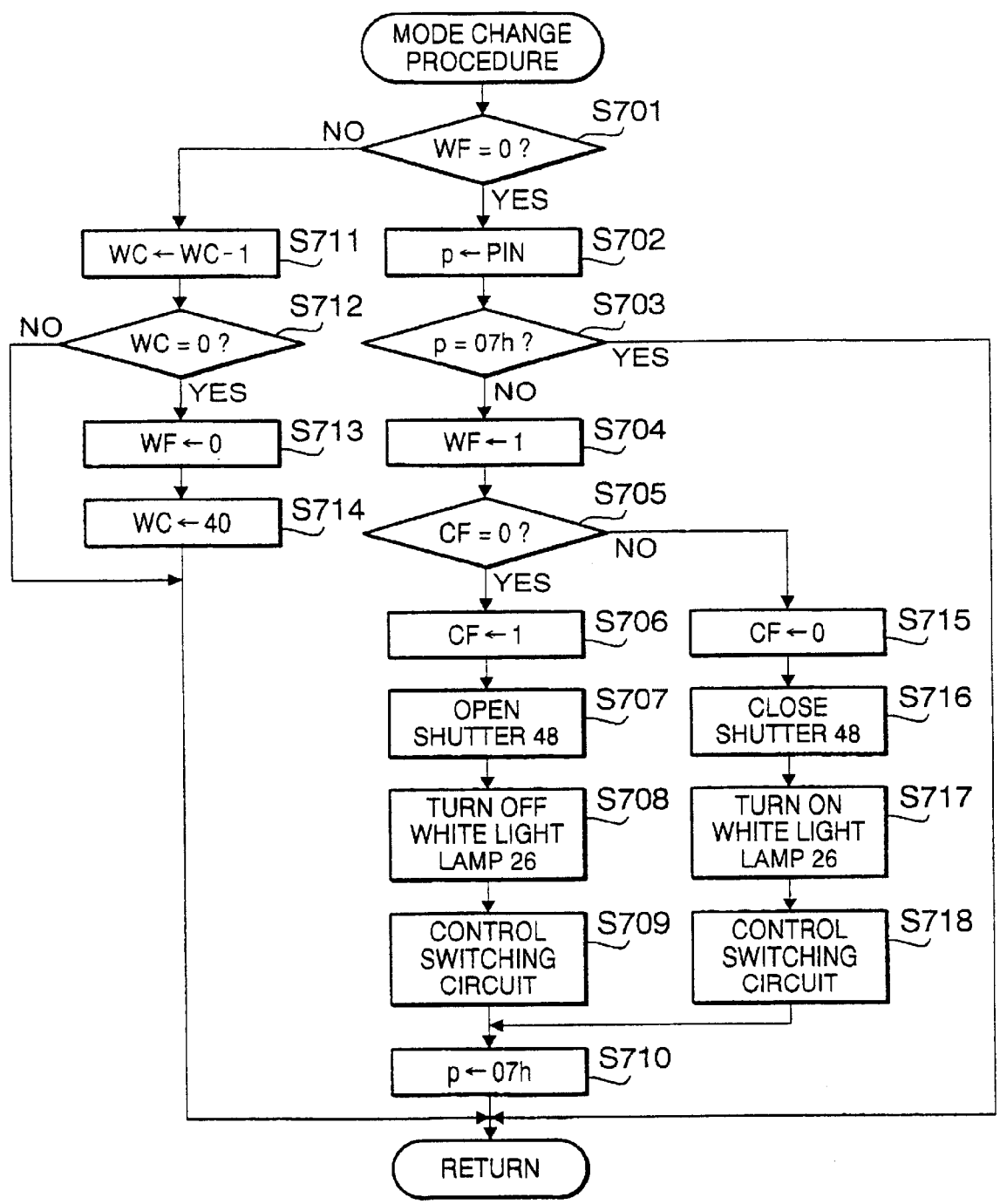
FIG. 7 is a flowchart of mode change procedure according to the first embodiment.

FIG. 7 is a flowchart illustrating the mode changing procedure. The mode changing procedure is an interruption procedure which is executed at every predetermined interval (e.g., 50 ms.). The mode change procedure is allowed to interrupt when the light switch 80 is turned ON. It should be noted that, in the first embodiment, when the light switch 80 is turned ON, both the white light source 26 and the UV lamp 38 are turned ON.

At S701, it is detected whether the flag WF is zero (0) or one (1). At an initial stage, the flag WF is set to zero (S701: YES), and control proceeds to S702. At S702, current hexadecimal value $P_{IN}$ of the input port is detected, and the variable p is set to the detected value.

At S703, it is detected whether the variable p is equal to 07h, i.e., it is detected whether one of the mode switches 78, 88, 90 or 92 is operated. If p is equal to 07h (S703: YES), none of the mode switches are operated, and the interruption procedure is terminated. At every 50 ms, the interruption procedure is executed. If none of the mode switches 78, 88, 90 and 92 is operated, the variable p stays 07h, and no substantial operation related to the mode change is performed during the interruption procedure.

At S703, if it is detected that the variable p is not equal to 07h, i.e., if one of the mode switches 78, 88, 90 and 92 is operated (S703: NO), control proceeds to S704, where the flag WF is set to one (1). At S705, it is determined whether the flag CF is zero (0) or one (1). At the initial stage, the CF is set to zero (S705: YES), control proceeds to S706, where the flag CF is set to one (1), which means the fluorescent image mode is selected. Then, the shutter 48 is opened (S707), the white light source 26 is turned OFF (S708), and the switching circuit 58 is set to connect the second input system 56 to the A/D converter 60 (S709). At S710, the variable p is reset to 07h, and the mode change procedure is terminated.

After 50 ms has passed, the mode change procedure is executed again. At this stage, since the flag WF has been set to one (1), control proceeds from S701 to S711, where the counter WC (which has been set to forty) is decremented by one. Then, at S712, it is determined whether the counter WC is equal to zero (0). If the counter WC is greater than zero (S712: NO), the mode change procedure is terminated. Until the counter WC is equal to zero, every time when the mode change procedure is executed at 50 ms interval, control proceeds from S701 to S711 regardless of the operation status of the mode switches 78, 88, 90 or 92, and the counter WC is decremented by one. Thus, once the mode switches 78, 88, 90 or 92 is operated (S703: NO), operation of the mode switches 78, 88, 90 and 92 is ignored or invalidated for a certain period therefrom. In this embodiment, since the counter WC is set to forty, and the interruption procedure is executed at every 50 ms, the period during which the operation of the switches 78, 88, 90 and 92 is ignored after the operation mode is switched between the color image mode and the fluorescent image mode is two seconds.

As the mode change procedure is repeatedly executed and the counter WC is equal to zero (S712: YES), the flag WF is set to zero (0) at S713, and the counter WC is set to forty (S714), then the procedure is terminated. Thereafter, when the mode change procedure is executed, control proceeds from S701 to S702. However, if none of the mode switches 78, 88, 90 and 92 is operated, determination at S703 is "YES", and the procedure is terminated.

At S703, if it is detected that the variable p is not equal to 07h, i.e., if one of the mode switches 78, 88, 90 and 92 is operated (S703: NO), control proceeds to S704, where the flag WF is set to one (1). At S705, it is determined whether the flag CF is zero (0) or one (1). At this stage, the CF is set to one (S705: NO), and control proceeds to S715, where the flag CF is set to zero (0), which means the color image mode is selected. Then, the shutter 48 is closed (S716), the white light source 26 is turned ON (S717), and the switching circuit 58 is set to connect the first input system 54, to the A/D converter 60 (S718). At S710, the variable p is reset to 07h, and the mode change procedure is terminated.

After 50 ms has passed, the mode change procedure is executed again. At this stage, as described above, since the flag WF has been set to one (1), control proceeds from S701 to S711, where the counter WC (which has been set to forty) is decremented by one. Then, at S712, it is determined whether the counter WC is equal to zero (0). If the countet WC is greater than zero (S712: NO), the mode change procedure is terminated. Until the counter WC is equal to zero, every time when the mode change procedure is executed at 50 ms interval, control proceeds from S701 to S711 regardless of the operation status of the mode switches 78, 88, 90 or 92, and the counter WC is decremented by one. Thus, after the mode switch 78, 88, 90 or 92 has been operated (S703: NO), operation of the mode switches 78, 88, 90 and 92 is ignored or invalidated for two seconds.

As above, according to the first embodiment, when one of the mode switches 78, 88, 90 and 92 is operated, the operation mode is immediately switched between the color image mode and the fluorescent image mode, and various operations/setting of the endoscope system 1000, such as the change of the light source, in association with the change of the operation mode can be performed without fail.

Second Embodiment

Figure 8:
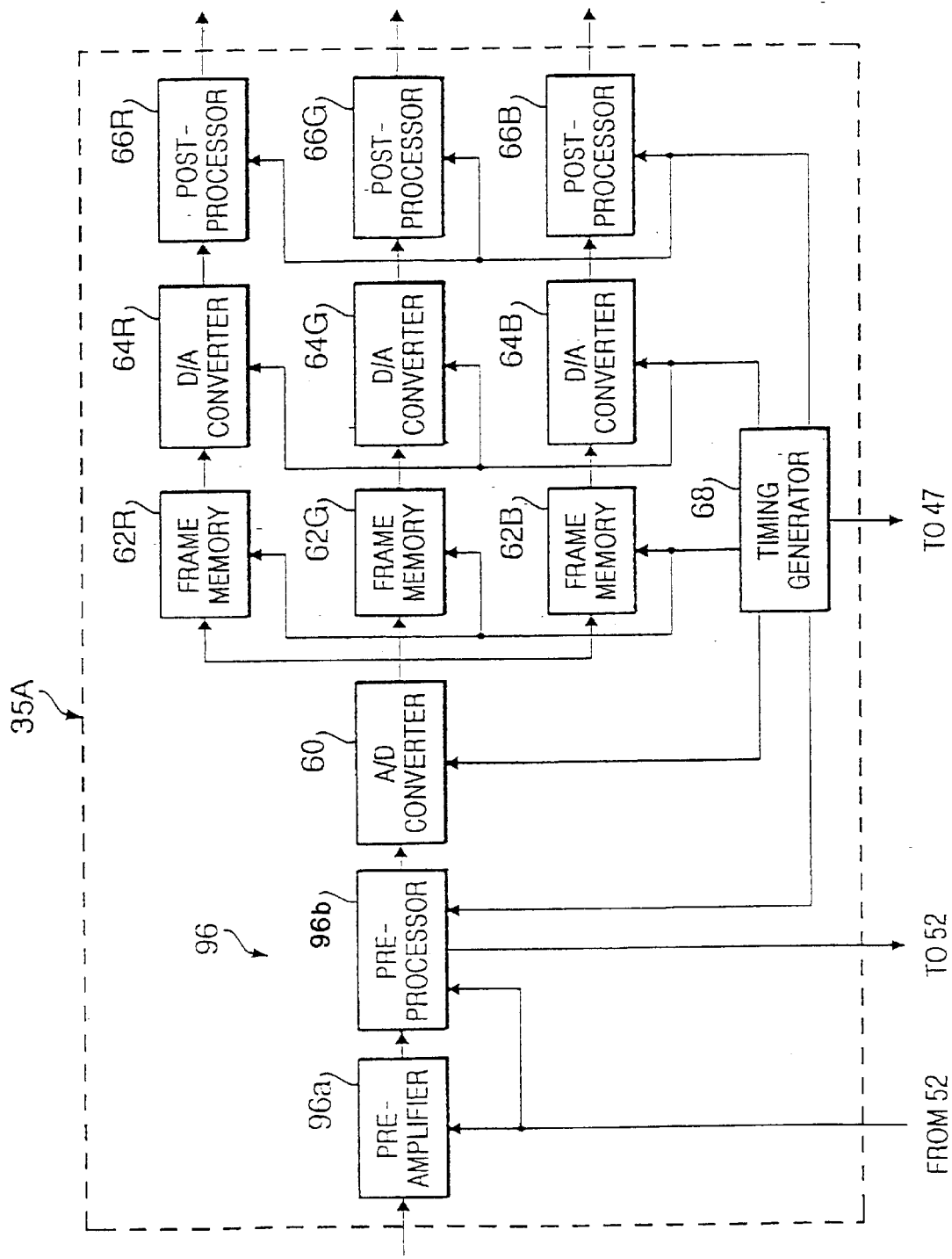
FIG. 8 is a block diagram of the image signal processing unit according to a second embodiment of the invention, which can be employed in the electronic endoscope system shown in FIG. 1.

FIG. 8 shows an image signal processing circuit 35A according to a second embodiment of the invention. The elements similar to those of the image signal processing circuit 35 shown in FIG. 4 are assigned with the same numbers and description thereof is omitted for the sake of the simplicity.

In the image signal processing circuit 35A, instead of the first and second input systems 54 and 56 of the first embodiment shown in FIG. 4, a single input system 96 is provided. The input system 96 includes a pre-amplifier 96a and a pre-processor 96b, the output terminal of which is connected to the input terminal of the A/D converter 60 without a switching circuit. In the second embodiment, the pre-amplifier 96a is a VCA (voltage-controlled amplifier) whose gain is controlled in accordance with the voltage applied thereto by the system controller 52. That is, the gain of the pre-amplifier 96a is controlled depending on which of the color image mode and the fluorescent image mode is selected.

Similarly, characteristics of the pre-processor 96b, which applies image processing operations to the image signals amplified by the pre-amplifier 96a, are changeable depending on which of color image mode and the fluorescent image mode is selected.

When the color image mode is selected, a frame of analog pixel signals for each color are transmitted from the CCD 16, through the input system 96, to the A/D converter 60. Then, the analog pixel signals are converted into digital pixel signals. Thereafter, the color video signal is generated and output by the image signal processing circuit 35A to the monitor device, as is performed in the first embodiment.

When the fluorescent image mode is selected, a frame of analog pixel signals are transmitted from the CCD 16, through the input system 96, to the A/D converter 60. Then, the analog pixel signals are converted into digital pixel signals. Thereafter, the monochromatic video signal is generated and output by the image signal processing circuit 35A to the monitor device, similarly to the first embodiment.

Third Embodiment

Figure 9:
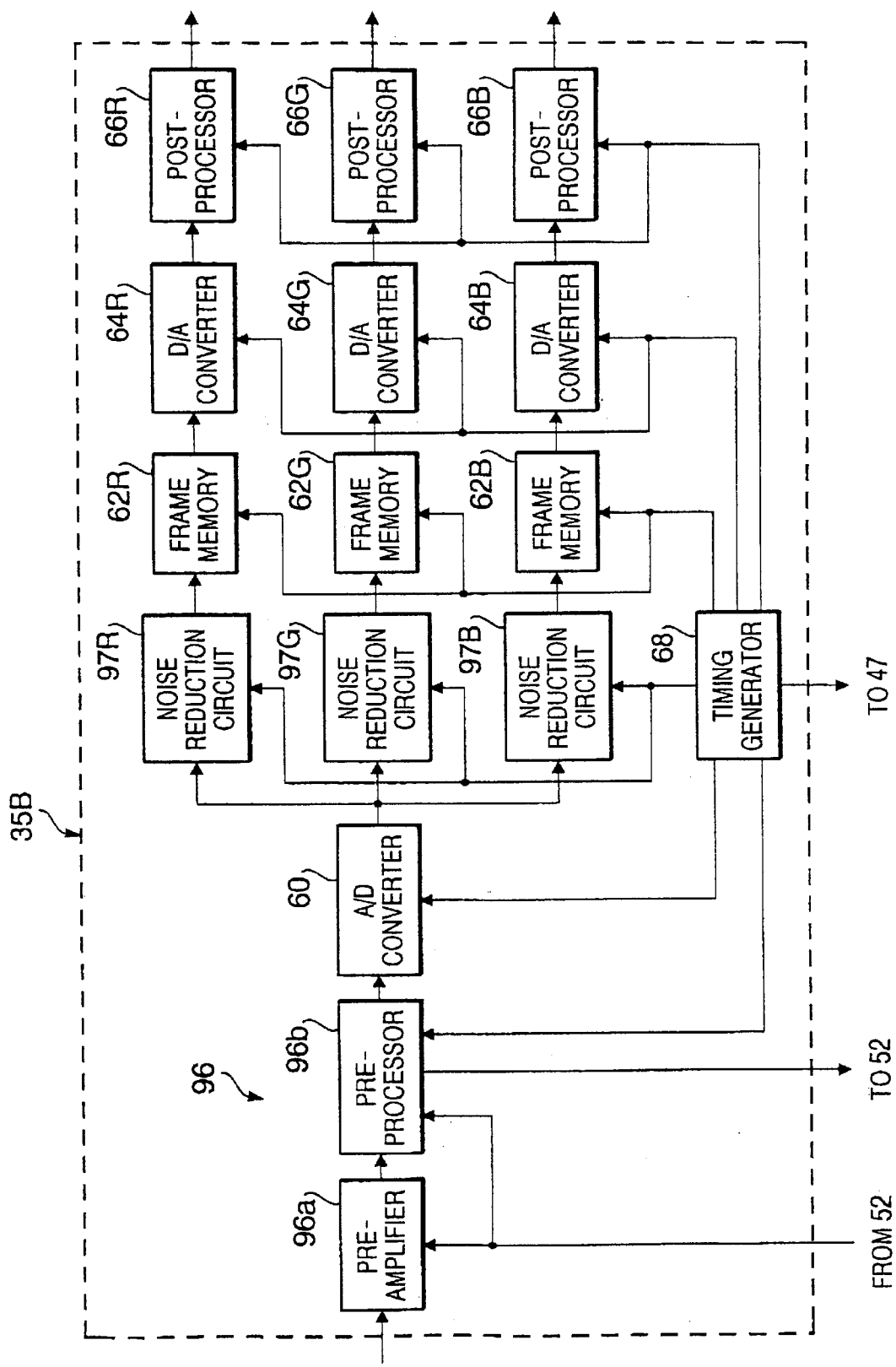
FIG. 9 is a block diagram of the image signal processing unit according to a third embodiment of the invention, which can be employed in the electronic endoscope system shown in FIG. 1.

FIG. 9 shows an image signal processing circuit 35B according to a third embodiment of the invention. The image signal processing circuit 35B is substantially similar to the image signal processing circuit 35A shown in FIG. 8 except that noise reduction circuits 97R, 97G and 97B are inserted between the A/D converter 60 and the frame memories 62R, 62G and 62B.

As aforementioned, the sensitivity of the CCD 16 is relatively low with respect to the fluorescent light, whose wavelength is relatively short. Therefore, when the fluorescent image mode is selected, the gain of the pre-amplifier 96a should be made greater than that when the color image mode is selected. Due to the relatively high gain of the pre-amplifier, the noise included in the analog pixel signals are also amplified at the high gain when the fluorescent image mode is selected. For reducing such noise, the noise reduction circuits 97R, 97G and 97B are provided.

As described before, the image signal processing circuit 35B is originally designed for generating three primary color video signals, and according to the invention, by slightly modifying such a circuit, the monochromatic video signal is generated when the fluorescent image mode is selected. From the image signal processing circuit 35B, three monochromatic video signals can be output. If only one monochromatic video signal is used for displaying the fluorescent image using the signal through, for example, the frame memory 62G, D/A converter 64G and the post-processor 66G, only one noise reduction circuit 97G is used, and the other noise reduction circuits 97R and 97B may be omitted.

It should be noted that the noise reduction circuit(s) 97R, 97G and/or 97B may be added to the image signal processing circuit 35, shown in FIG. 4.

Figure 10:
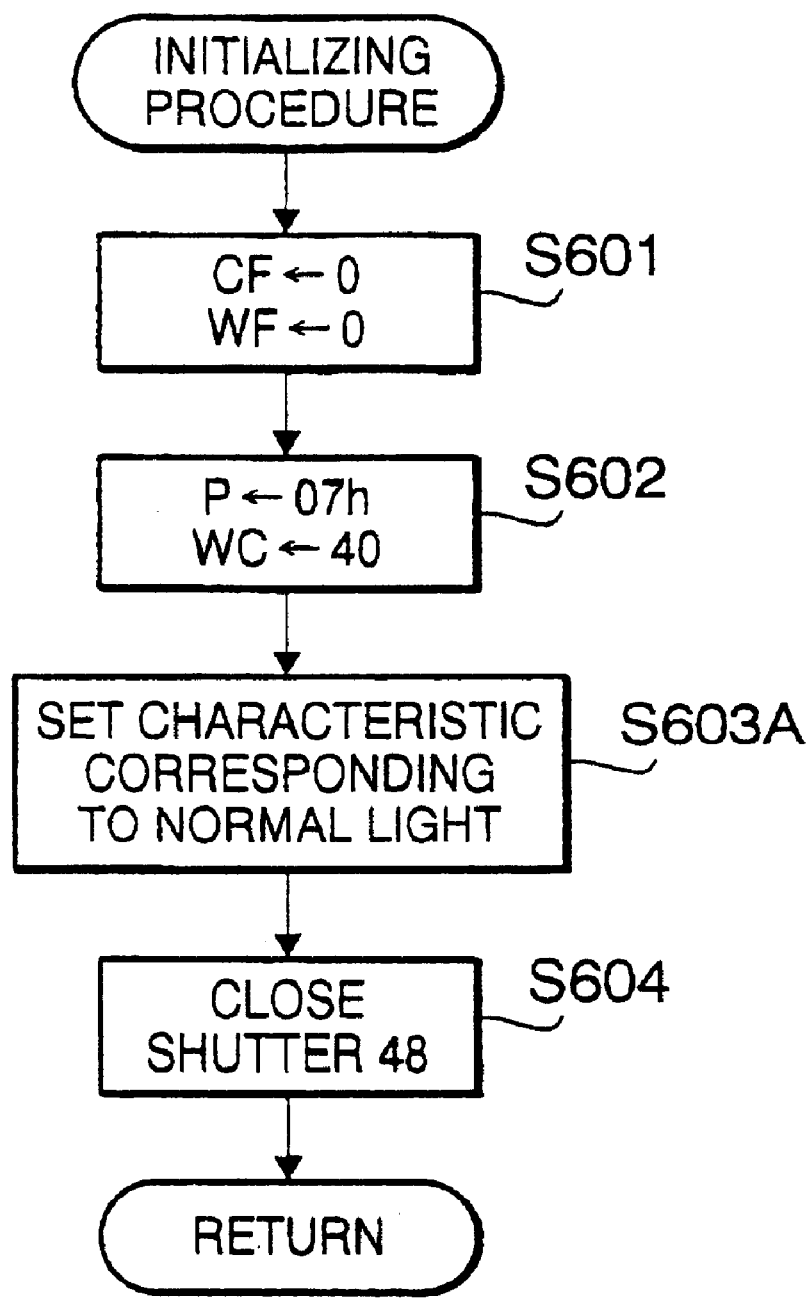
FIG. 10 is a flowchart of an initializing procedure according to the second or third embodiment.

When the image signal processing circuit 35A or 35B is used in the endoscope system 1000 shown In FIG. 1, the initial procedure shown in FIG. 6 should be change as the modified procedure shown in FIG. 10, in which step S603 is replaced with step S603A. At step S603A, the gain of the pre-amplifier 96a and the characteristics of the pre-processor 96b are set suitable for the color image mode.

Figure 11:
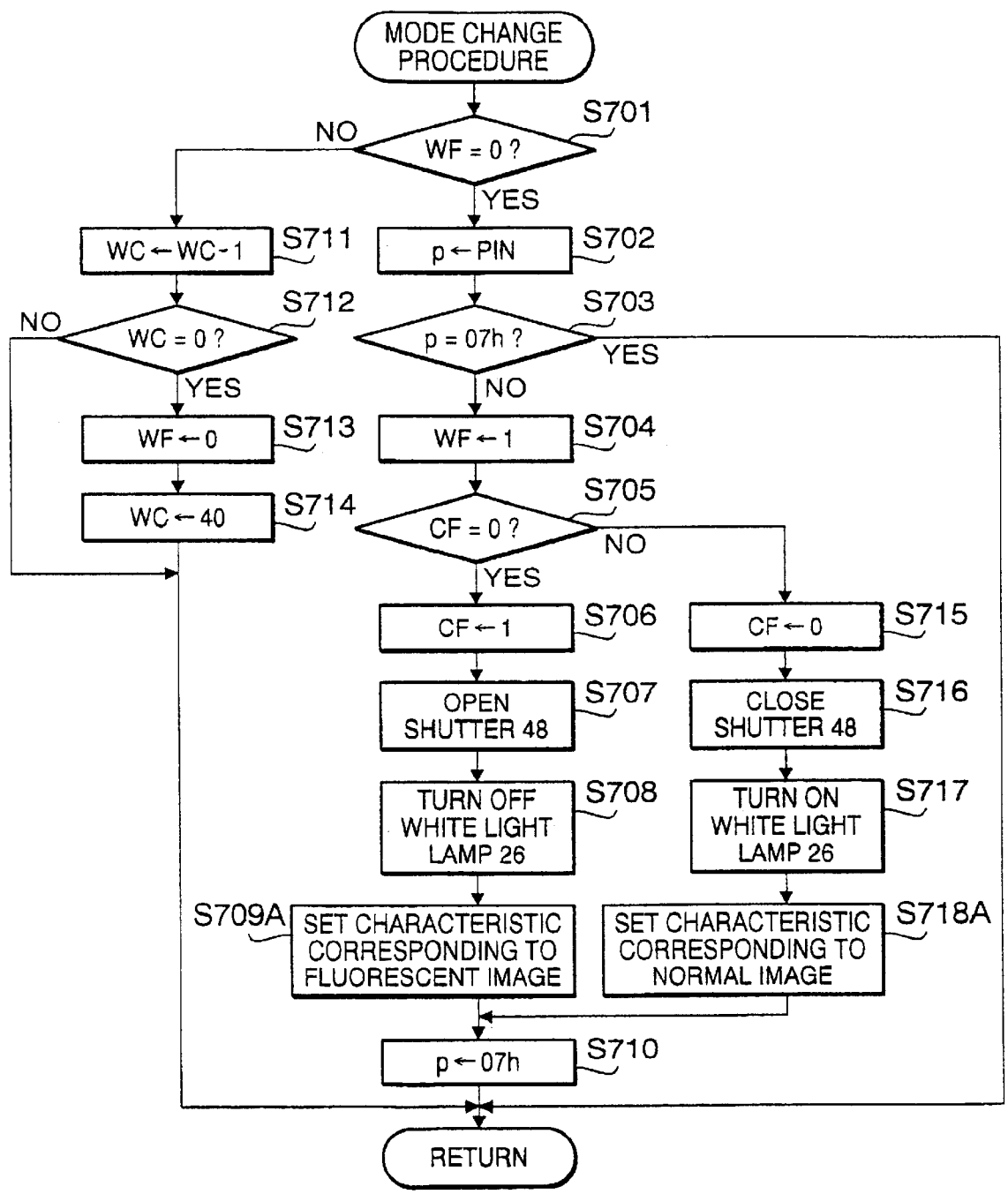
FIG. 11 is a flowchart of mode change procedure according to the second or third embodiment.

Further, when the image signal processing circuit 35A or 35B is used in the endoscope system 1000 shown in FIG. 1, the mode change procedure shown in FIG. 7 should be modified as shown in FIG. 11, where steps S709 and S718 are replaced with steps S709A and S718A. At step 709A, the gain of the pre-amplifier 96a and the characteristics of the pre-processor 96b are set suitable for the fluorescent image mode. At step 718A, the gain of the pre-amplifier 96a and the parameters for pre-processor 96b are set suitable for the color image mode.

Fourth Embodiment

Figure 12:
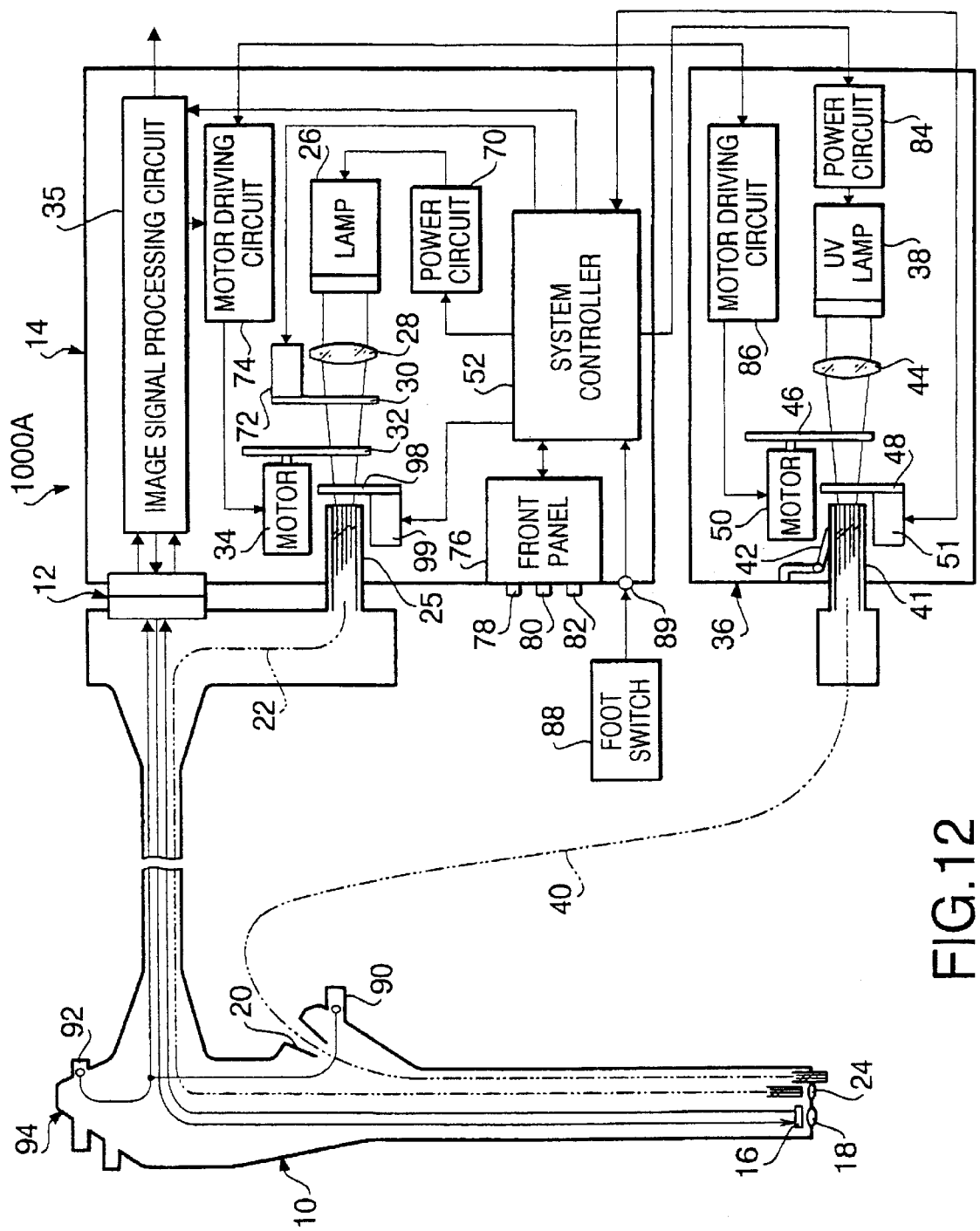
FIG. 12 is a block diagram of an electronic endoscope system according to a fourth embodiment of the invention.

FIG. 12 shows an endoscope system 1000A according to a fourth embodiment of the present invention. The endoscope system 1000A is similar to the endoscope system 1000 shown in FIG. 1 except that a shutter 98 is provided between the proximal end surface of the light guide cable 22 and the rotary filter 32, and an actuator 99 for driving the shutter 98.is provided. The shutter 98 shields/transmits the light directed from the rotary filter 32 to the proximal end surface of the light guide cable 22. When the color image mode is selected, the shutter 98 is opened (i.e., transmits the light), while when the fluorescent image mode is selected, the shutter 98 is closed (i.e., the light does not incident on the proximal end surface of the light guide cable 22). Further, the white light source 26 remains to be turned ON even in the fluorescent image mode is selected. That is, when the color image mode is selected, the shutter 98 is opened to allow the light passed through the rotary filter 32 to be incident on the proximal end surface of the light guide cable 22, while the shutter 48 is closed. When the fluorescent image mode is selected, the shutter 48 is opened, while the shutter 98 is closed. It should be noted that the actuator 99, which drives the shutter 98, is controlled by the system controller 52.

According to the above configuration, when the operation mode is switched from the fluorescent image mode to the color image mode, stable light emission from the white light source 26 is ensured since it is kept turned ON, and accordingly, a color image can be observed on the monitor device immediately when the operation mode is switched to the color image mode. Further, even though the color image mode and the fluorescent image mode are switched frequently, the white light source 26 is not frequently turned ON/OFF. Therefore, the life of the white light source 26 can be elongated.

Figure 13:
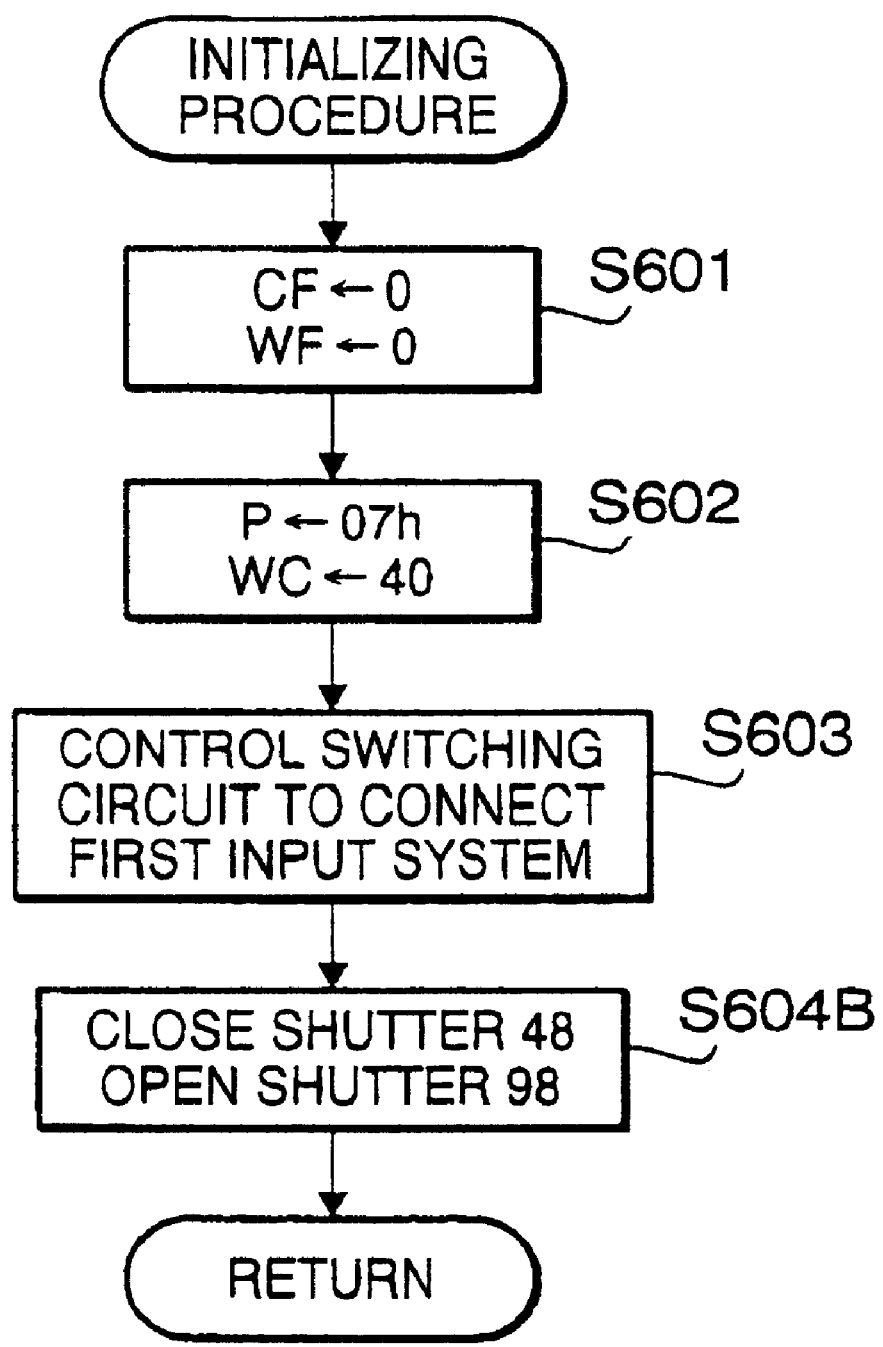
FIG. 13 is a flowchart of an initializing procedure according to the fourth embodiment of the invention.

If the endoscope system 1000A is provided with the image signal processing circuit 35 shown in FIG. 4, the initializing procedure shown in FIG. 6 should be modified to the procedure shown in FIG. 13. Specifically, step S604 should be replaced with step S604B, at which the shutter 48 is closed and the shutter 98 is opened.

Figure 14:
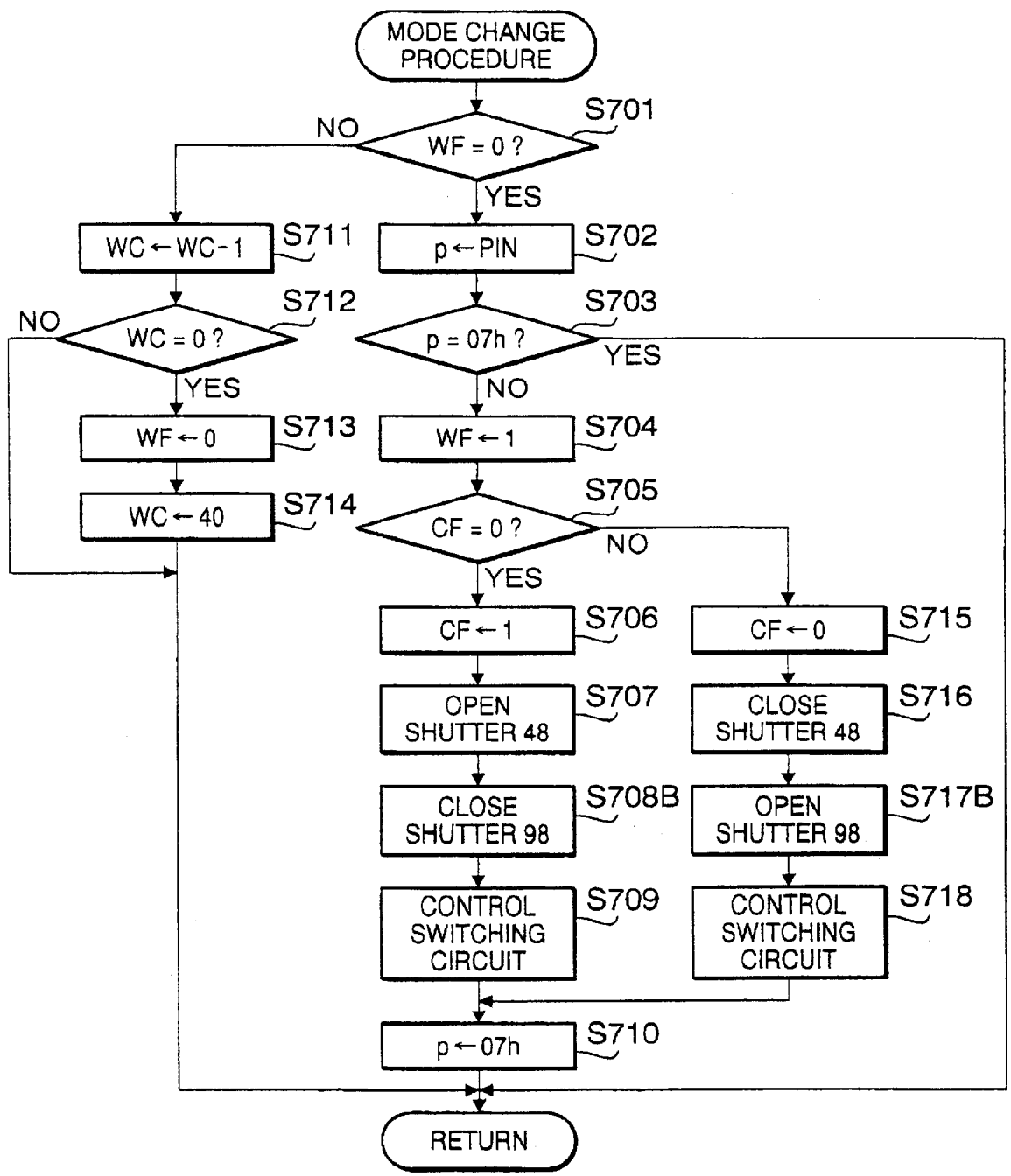
FIG. 14 is a flowchart of mode change procedure be according to the fourth embodiment.

Further, the mode change procedure shown in FIG. 7 should be modified to a procedure shown in FIG. 14. Specifically, step S708 is replaced with steps S708B, where the shutter 98 is closed, and step S717 is replaced with S717B, where the shutter 98 is opened.

Figure 15:
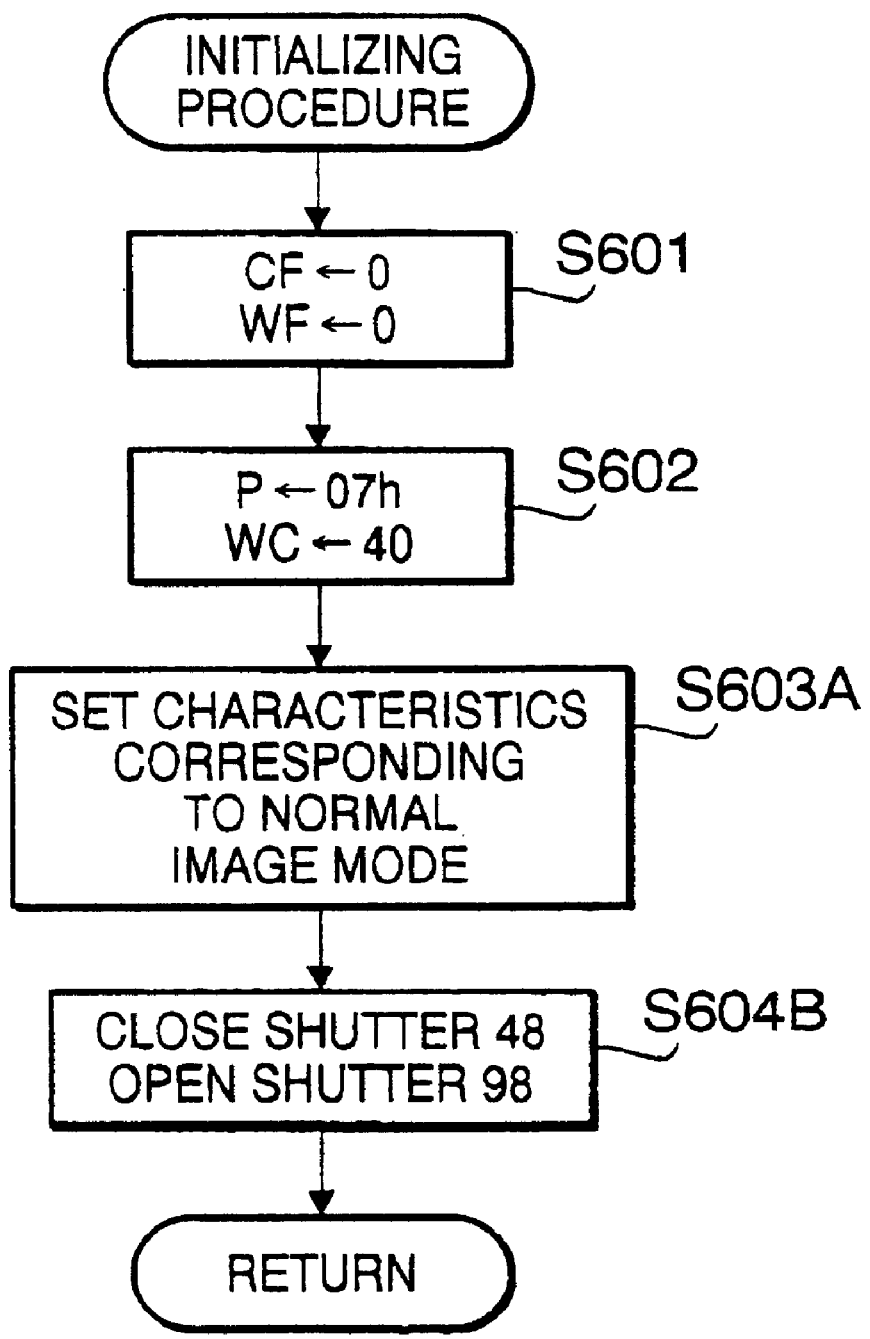
FIG. 15 is a flowchart of an initializing procedure according to a modification of the fourth embodiment.

If the endoscope system 1000A is provided with the image signal processing circuit 35A or 35B shown in FIG. 8 or 9, the initializing procedure shown in FIG. 10 should be modified to the procedure shown in FIG. 15. Specifically, step S604 should be replaced with step S604B, at which the shutter 48 is closed and the shutter 98 is opened.

Figure 16:
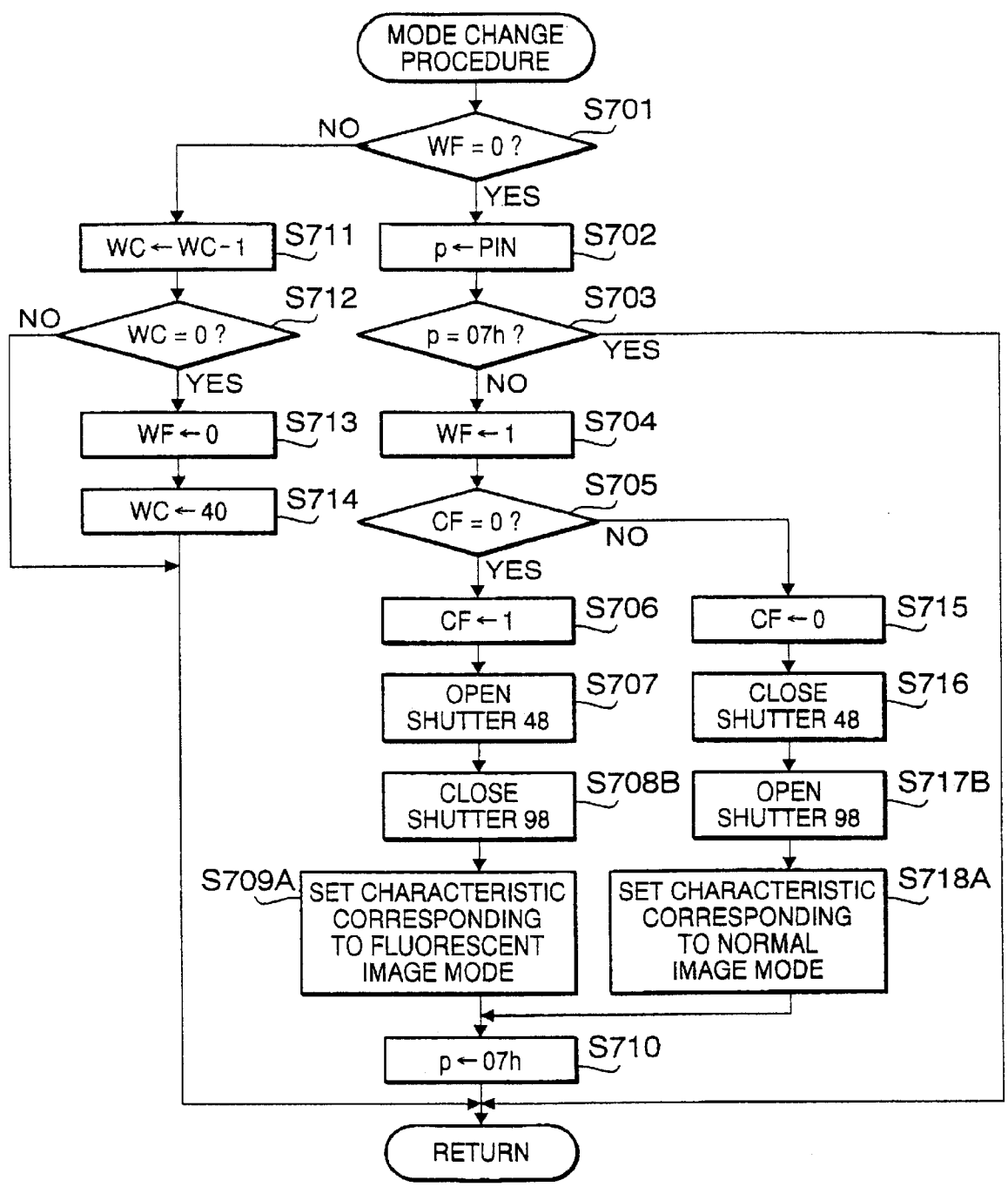
FIG. 16 is a flowchart of mode change procedure according to the modification of the fourth embodiment.

Further, the mode change procedure shown in FIG. 11 should be modified to a procedure shown in FIG. 16. Specifically, steps S708 and S717 are replaced with steps S708B, where the shutter 98 is closed, and S717B, where the shutter 98 is opened.

Fifth Embodiment

Figure 17:
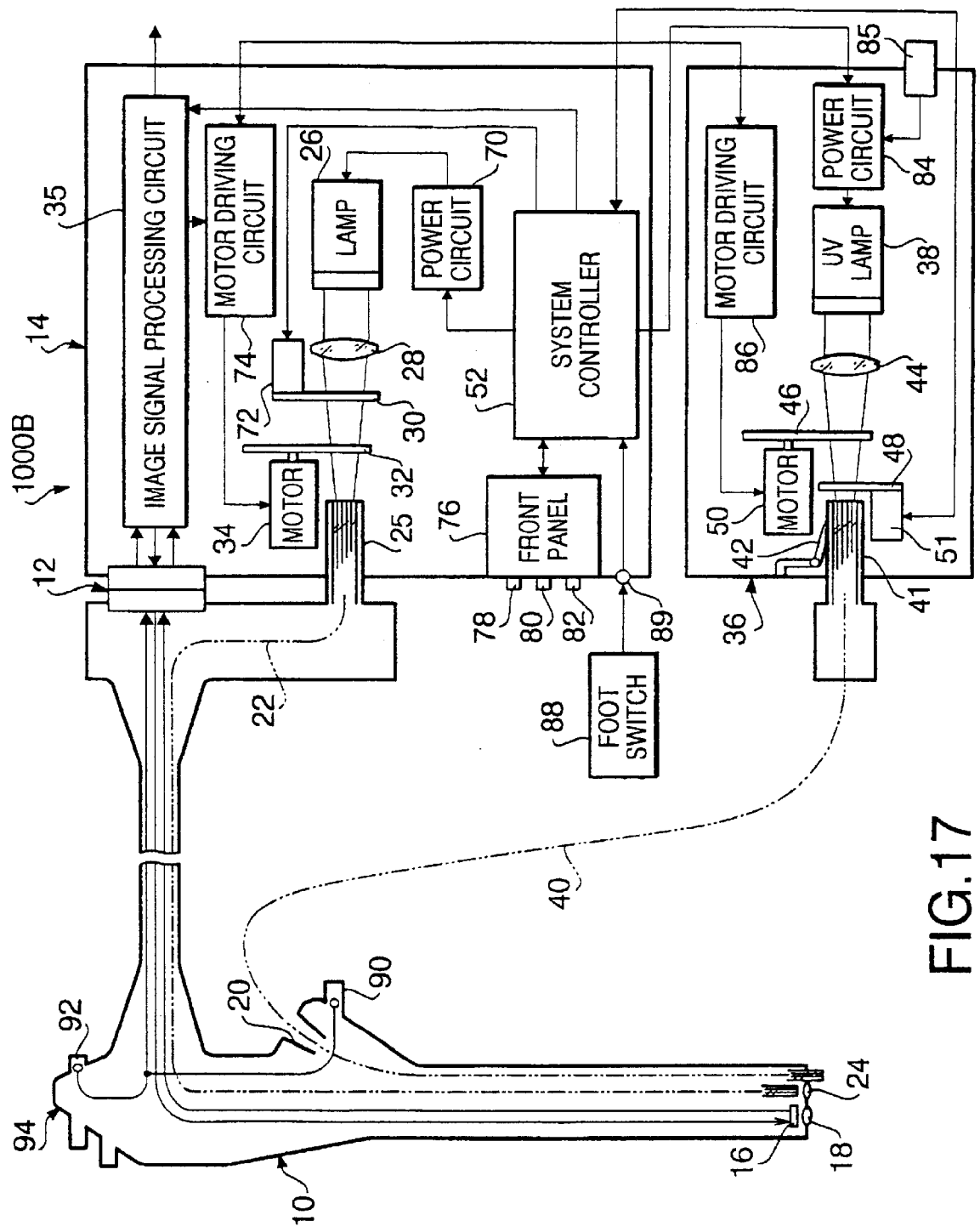
FIG. 17 is a block diagram of an electronic endoscope system according to a fifth embodiment of the invention.

FIG. 17 is a block diagram showing an electronic endoscope system 1000B according to a fifth embodiment. The configuration of the electronic endoscope system 1000B is similar to that of the electronic endoscope system 1000 shown in FIG. 1 except that a power switch 85 for turning ON/OFF the UV lamp 38 is provided on a housing of the UV light source unit 36. Specifically, when the power switch 85 is operated to turn ON the power source circuit 84 is turned ON and the UV lamp 38 is lit, and when the power switch 85 is operated to turn OFF the power source circuit 84 and the UV lamp is turned OFF. It should be noted, go however, the ON/OFF control of the UV lamp 38 can be performed in another way, which will be described later. The same reference numerals as referred to in the first embodiment are assigned to the elements similar to those employed in the first embodiment, and description thereof will be omitted.

Figure 18:
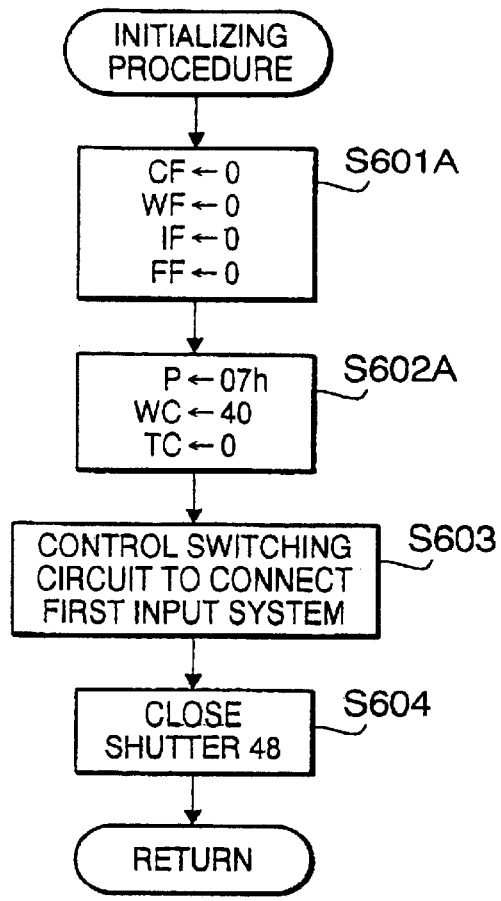
FIG. 18 is a flowchart of an initializing procedure according to the fifth embodiment.

FIG. 18 is a flowchart illustrating an initializing procedure according to the fifth embodiment, which is executed when the power switch 82 is turned ON. The initializing procedure shown in FIG. 18 is similar to the procedure shown in FIG. 6 except that steps S601 and S602 are slightly modified to S601A and S602A.

At S601A, as in the first embodiment, flags CF and WF are initialized (i.e., set to zero (0)). Further, flags IF and FF are initialized, i.e., set to zero (0).

Figure 19:
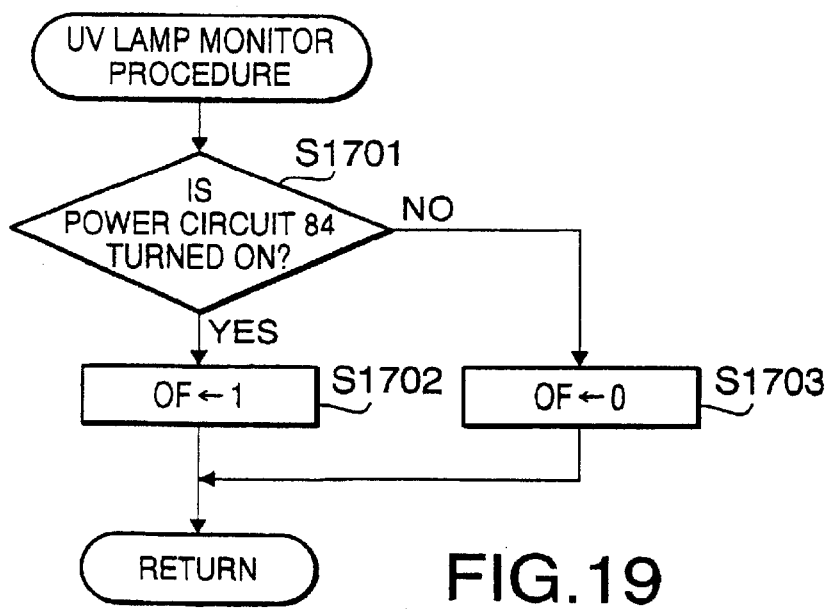
FIG. 19 is a flowchart of UV lamp monitoring procedure according to the fifth embodiment.
Figure 20:
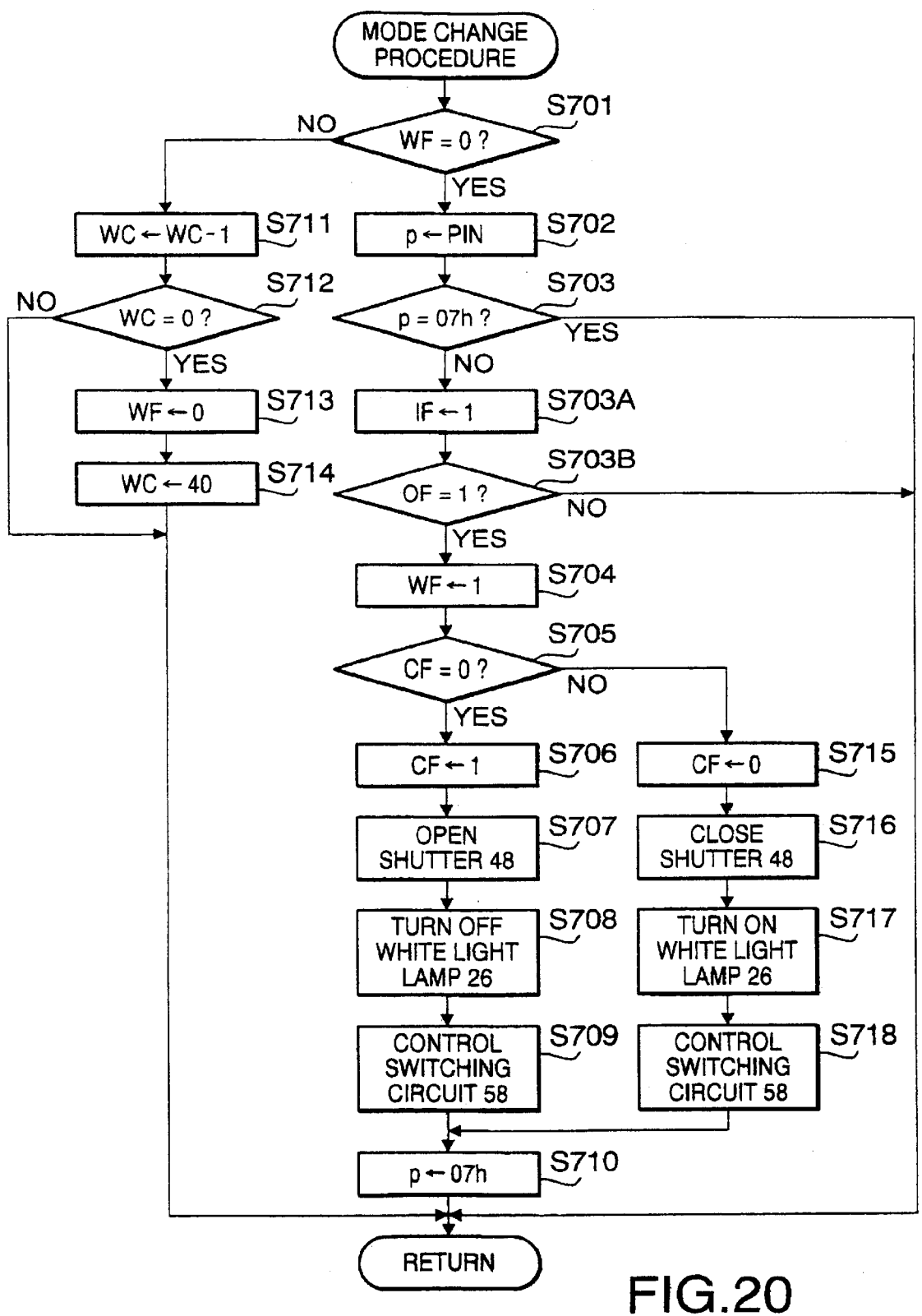
FIG. 20 is a flowchart of a mode change procedure according to the fifth embodiment.

The flag IF is referred when a mode change procedure shown in FIG. 19 is performed. The flag IF represents whether an UV lamp ON/OFF procedure, which is an interruption procedure, is allowed to interrupt. Specifically, the flag IF is set to one (1) when one of the mode switches 78, 88, 90 and 92 is operated. When flag IF is equal to one (1), an interruption signal is input to the CPU of the system controller 52 at every predetermined period, e.g., one second. Then, at every occurrence of the interruption signal, the UV lamp ON/OFF procedure shown in FIG. 20 is executed once.

The flag FF is referred to in the LTV lamp ON/OFF procedure. The flag FF is used for optimizing time measurement using a time measurement counter TC.

At S602A, as in the first embodiment, a variable p is set to 07h as an initial value, and a counter WC is set to forty

(40) as an initial value. Further, the time measurement counter TC is reset to zero (0). The time measurement counter TC is used for measuring a duration of time during which one of the mode switches 78, 88, 90 and 92 is operated.

FIG. 19 is a flowchart illustrating the UV lamp monitoring procedure. The UV lamp monitoring procedure is executed by the CPU of the system controller 52. The UV lamp monitoring procedure is an interruption procedure, which is executed at every predetermined interval, e.g., one second, while the power switch 82 is turned ON.

At step S1701, it is detected whether the power circuit 84 is an ON state or OFF state. That is, whether the UV lamp 38 is turned ON or OFF is detected. If the UV lamp 38 is turned ON (S1701: YES), the status flag OF is set to one (1) (S1702). If the UV lamp 38 is OFF (S1701: NO), the status flag OF is set to zero (0) at S1703. Thus, by referring to the status flag OF, the ON/OFF status of the UV lamp 38 can be detected.

FIG. 20 is a flowchart illustrating a mode change procedure according to the fifth embodiment of the invention. The procedure shown in FIG. 20 is similar to the procedure shown in FIG. 8 except that steps S703A and S703B are inserted after S703.

Control proceeds from S703 to S703A when it is determined that the variable p is not equal to 07h (S703: NO), i.e., one of the switches 78, 88, 90 and 92 is operated. At S703A, the flag IF.is set to one (1) to allow the UV lamp ON/OF procedure to interrupt. At S703B, it is detected whether the status flag OF is equal to one (1). If the status flag OF is equal to zero (0), i.e., if the UV lamp 38 is turned OFF (S703B: NO), the illumination light source cannot be switched, and the procedure is terminated. That is, when the UV lamp 38 is turned OFF, even if the mode switch 78, 88, 90 or 92 is operated, the operation is invalidated or ignored. If the status flag OF is equal to one (1), i.e., if the UV lamp 38 is turned ON (S703B: YES), control proceeds to S704. Thereafter, procedures similar to those in the first embodiment are executed.

If one of the switches 78, 88, 90 and 92 is operated after the illumination has been changed to the UV light illumination, and control proceeds from S703 to S703A, the flag IF is set to one (1). Then, at S703B, the status flag OF is checked. At this stage, since the UV lamp 38 has been used for illumination light source, control proceeds to S704.

Figure 21:
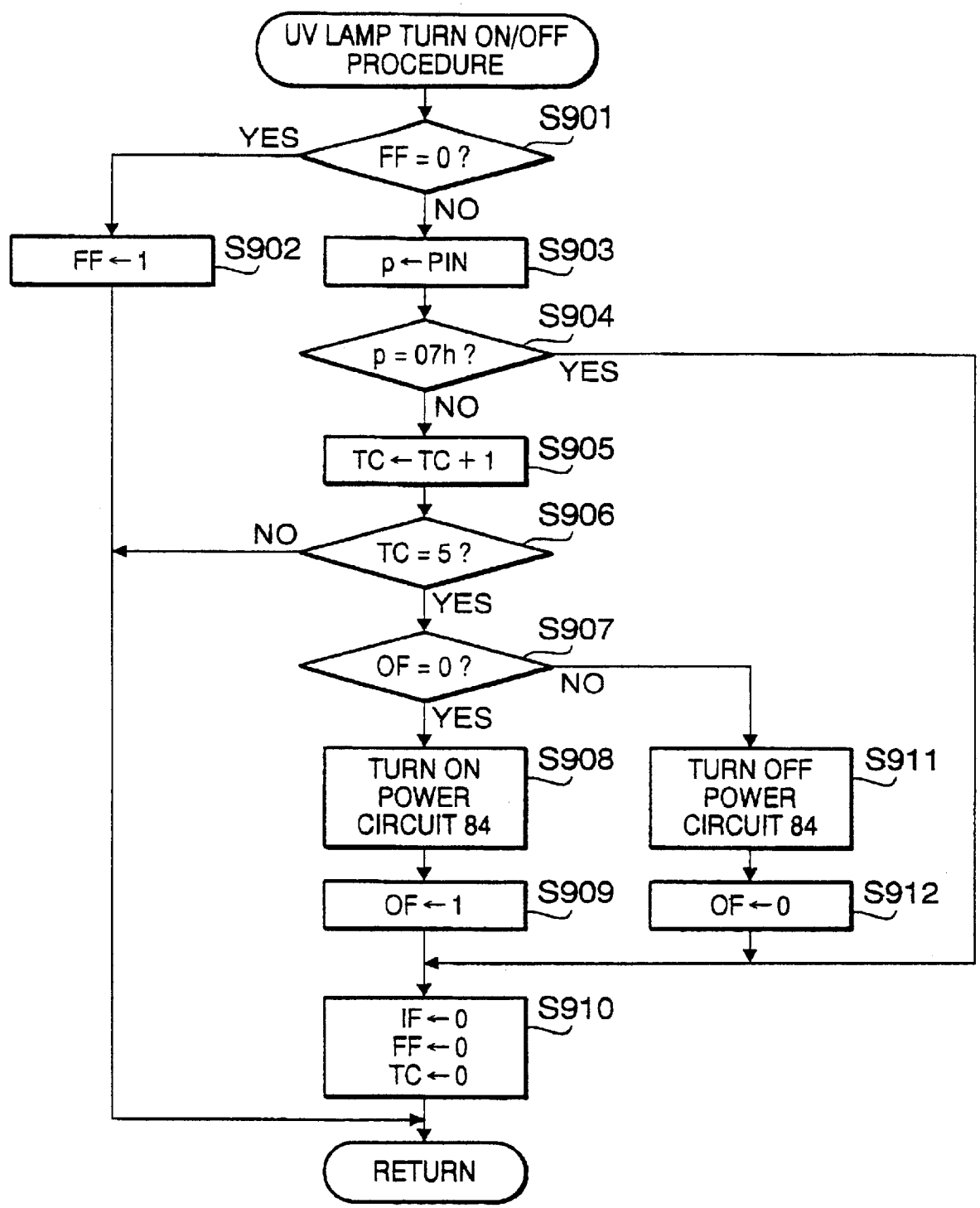
FIG. 21 is a flowchart of a UV lamp ON/OFF procedure according to the fifth embodiment.

FIG. 21 is a flowchart illustrating the UV lamp ON/OFF procedure. This procedure is an interruption procedure, which is executed at every one second after the flag IF is set to one (1) at step S703A of FIG. 20.

At S901, it is determined whether the time measurement optimizing flag FF is equal to zero (0) or one (1). At an initial stage, the flag FF is zero (see FIG. 18), and therefore, control proceeds to S902, where the flag FF is set to one (1), and the procedure is terminated.

The procedure is executed again, when one second has elapsed, control proceeds from S901 to S903, where the hexadecimal number P$_{IN}$ of the input port is read, which is given to the variable p. At step S904, it is detected whether the variable p is equal to 07h. If the variable p is not equal to 07h (S904: NO), one of the switches 78, 80, 90 and 92 is kept operated, and control proceeds to S905, where the counter TC is incremented by one (1). At S906, it is detected whether, the counter TC has reached five (5). If the counter TC is less than five (S906: NO) the procedure is terminated.

At every one second, the procedure is repeated. If one of the switches 78, 88, 90 and 92 is kept operated, the above described procedure is repeated until the counter TC reaches five.

If one of the switches 78, 88, 90 and 92 is kept operated, and the counter TC has reached five, i.e., if one of the mode switches 78, 88, 90 and 92 is kept operated for five seconds (S906: YES), the status flag OF is checked at S907. If the status flag OF is equal to zero (0), i.e., if the UV lamp is turned OFF (S907: YES), control proceeds to S908, where the power circuit 84 is turned ON and accordingly, the UV lamp 38 is turned ON. At S909, the status flag OF is set to one (1). Then, at S910, the flags IF and FF are reset to zero, and the counter is also reset to zero, and the procedure is terminated. Since the flag IF is set to zero at S910, interruption of the UV lamp ON/OFF procedure is inhibited until one of the mode switches 78, 88, 90 and 92 is operated and the flag IF is set to one (1) again.

If it is determined that the status flag OF is equal to one (1) at S907, i.e., if the UV lamp 38 is turned ON (S907: NO), control proceeds to S911, where the power circuit 84 is turned OFF, and accordingly, the UV lamp is turned OFF. Then, at S912, the status flag OF is set to zero (0), and control proceeds to S910. As described above, at S910, the flags IF and FF are reset to zero, the counter is also reset to zero, and the procedure is terminated. Since the flag IF is set to zero at S910, interruption of the UV lamp ON/OFF procedure is inhibited until one of the mode switches 78, 88, 90 and 92 is operated and the flag IF is set to one (1) again.

If it is detected, at S904, that the variable p is equal to 07h (S904: YES), i.e., if the operation of one of the mode switches 78, 88, 90 and 92 is terminated before the counter reaches five, control proceeds to S910. Also in this case, the flags IF and FF are reset to zero, and the counter is also reset to zero, and the procedure is terminated. Since the flag IF is set to zero at S910, interruption of the UV lamp ON/OFF procedure is inhibited until one of the mode switches 78, 88, 90 and 92 is operated and the flag IF is set to one (1) again.

As described above, according to the fifth embodiment, if the UV lamp 38 is turned OFF, it can be turned ON by holding one of the mode switches 78, 88, 90 and 92 operated for five seconds. If the operation of the switch 78, 88, 90 or 92 is terminated before five second has elapsed, the UV lamp remains turned OFF. On the contrarily, if the UV lamp 38 is turned ON, it can be turned OFF by holding one of the mode switches 78, 88, 90 and 92 operated for five seconds. If the operation of the switch 78, 88, 90 or 92 is terminated before five second has elapsed, the UV lamp remains turned ON.

Although the fifth embodiment is described as a modification of the first embodiment, any one of the second through fourth embodiment can also be modified to have the function of turning ON/OFF the UV lamp as in the fifth embodiment.

As described above, according to the fifth embodiment, the normal light and the light having a special wavelength as the illuminating light, and turning ON/OFF a light source of the light having the special wavelength can be done easily by the operator.

According to the fifth embodiment, in an electronic endoscope system, which uses the normal light and the light having a special wavelength as the illuminating light, and turning ON/OFF a light source of the light having the special wavelength can be done easily by the operator.

In the above-described embodiments, the UV lamp is used as an example of the special wavelength light source. The special wavelength light source is not limited to the UV lamp, but any other suitable light source may be alternatively or optionally employed.

In the embodiments, the special wavelength light source unit 36 is described as a unit separate from the image signal processing unit. However, the invention is not limited to such a constitution, and the special wavelength light source may be incorporated in the image signal processing unit.

The present disclosure relates to the subject matters contained in Japanese Patent Applications No. HEI 11-321026, filed on Nov. 11, 1999, and No. HEI 11-325305, filed on Nov. 16, 1999, which are expressly incorporated herein by reference in their entireties.

What is claimed is:

1. An electronic endoscope system including a scope unit for capturing an image of an object illuminated by light using an image sensor and an image processing unit that processes the captured image to generate a video signal, comprising:
   a first illuminating unit that illuminates the object with a first light having a first characteristic;
   a second illuminating unit that illuminates the object with a second light having a second characteristic;
   at least one switch that is operable to instruct a switching between said first illuminating unit and said second illuminating unit;
   a switcher that selects one of said first illuminating unit and said second illuminating unit in response to the operation of said at least one switch,
   said at least one switch being provided at a location accessible to an operator of said scope unit.

2. The electronic endoscope system according to claim 1, wherein said first illuminating unit includes:
   (a) a first light source that emits said first light; and
   (b) a first light guide cable extending through said scope unit to guide the first light from said first light source to a distal end of said scope unit,
wherein said second illuminating unit includes:
   (a) a second light source that emits said second light;
   (b) a second light guide cable extending through said scope unit to guide the second light from said second light source to the distal end of said scope unit; and
   (c) a shutter provided between said second light source and said second light guide cable,
      wherein, when said first illuminating unit is selected, said shutter is closed so that said second light is not guided by said second light guide cable, and
      wherein, when said second illuminating system is selected, said shutter is opened to allow said second light to be guided by said second light guide cable and said first light source is turned OFF.

3. The electronic endoscope system according to claim 1, wherein said first illuminating unit includes:
   (a) a first light source that emits light having a first characteristic;
   (b) a first light guide cable extending through said scope unit to guide the first light from said first light source to a distal end of said scope unit; and
   (c) a first shutter provided between said first light source and said first light guide cable,
wherein said second illuminating unit includes:
   (a) a second light source that emits light having a second characteristic;
   (b) a second light guide cable extending through said scope unit to guide the second light from said second light source to the distal end of said scope unit; and
   (c) a second shutter provided between said second light source and said second light guide cable,
      wherein, when said first illuminating unit is selected, said second shutter is closed so that said second light is not guided by said second light guide cable, and said first shutter is opened to allow said first light to be guided by said first light guide cable, and
      wherein, when said second illuminating unit is selected, said first shutter is closed so that said first light is not guided by said first light guide cable, and said second shutter is opened to allow said second light to be guided by said second light guide cable.

4. The electronic endoscope system according to claim 1, said first illuminating unit including a first light source that emits light having a first characteristic,
   said second illuminating unit including a second light source that emits light having a second characteristic,
   said electronic endoscope further comprising a controller that controls said second light source to turn ON and OFF,
   wherein if said second light source is turned OFF and said at least one switch is operated in a predetermined manner, said second light source is turned ON, and
   wherein if said second light source is turned ON and said at least one switch is operated in said predetermined manner, said second light source is turned OFF.

5. An electronic endoscope system including a scope unit for capturing an image of an object illuminated by light using an image sensor and an image processing unit that processes the captured image to generate a video signal, comprising:
   a first illuminating unit that illuminates the object with white light;
   a second illuminating unit that illuminates the object with light having a special wavelength;
   at least one switch that is operable to instruct a switching between said first illuminating unit and said second illuminating unit;
   a switcher that selects one of said first illuminating unit and said second illuminating unit in response to the operation of said at least one switch,
   said at least one switch being provided at a location accessible to an operator of said scope unit.

6. The electronic endoscope system according to claim 5, said at least one switch including a foot switch which is operable by a foot of the operator.

7. The electronic endoscope system according to claim 5, said scope unit being provided with an instrument channel through which a treatment tool is insertable, said at least one switch including a manually operable switch arranged adjacent to an inlet of said instrument channel.

8. The electronic endoscope system according to claim 7, said scope unit having an operation portion, at which operation switches are provided, said at least one switch including another manually operable switch arranged at said operation.

9. The electronic endoscope system according to claim 5, wherein said first illuminating unit includes:
   (a) a first light source that emits white light; and
   (b) a light guide cable extending through said scope unit to guide the white light from said first light source to a distal end of said scope unit,
wherein said second illuminating unit includes:
   (a) a special wavelength light source that emits light having a special wavelength;
   (b) another light guide cable extending through said instrument channel to guide the light having the special wavelength from said special wavelength light source to the distal end of said scope unit; and (c) a shutter provided between said special wavelength light source and said another light guide cable, wherein, when said first illuminating unit is selected using said at least one switch for illuminating the object, said shutter is closed so that the special wavelength light is not guided by said another light guide cable, and wherein, when said second illuminating unit is selected using said at least one switch for illuminating the object, said shutter is opened to allow the light having the special wavelength to be guided by said another light guide cable and said white light source if turned OFF.

10. The electronic endoscope system according to claim 5, wherein said first illuminating unit includes:

(a) a white light source that emits white light;

(b) a light guide cable extending through said scope unit to guide the white light from said white light source to a distal end of said scope unit; and (c) a first shutter provided between said white light source and said light guide cable, wherein said second illuminating unit includes:

(a) a special wavelength light source that emits light having a special wavelength;

(b) a second light guide cable extending through said instrument channel to guide the light having the special wavelength from said special wavelength light source to the distal end of said scope unit; and (c) a second shutter provided between said special wavelength light source and said second light guide cable, wherein, when said first illuminating unit is selected using said at least one switch for illuminating the object, said second shutter is closed so that the special wavelength light is not guided by said second light guide cable, and said first shutter is opened to allow the white light to be guided by said first light guide cable, and wherein, when said second illuminating unit is selected using said at least one switch for illuminating the object, said first shutter is closed so that the white light is not guided by said first light guide cable, and said second shutter is opened to allow the light having the special wavelength to be guided by said second light guide cable.

11. The electronic endoscope system according to claim 5, wherein a performance of said image processing unit is changed in accordance with the operation of said at least one switch so that an appropriate image processing operation is performed depending on a selected one of said first and second illuminating units.

12. The electronic endoscope system according to claim 11, said image processing unit includes an amplifier that amplifies image signals output by the image sensor, a gain of said amplifier when said second illuminating unit is selected being higher than a gain when said first illuminating unit is selected.

13. The electronic endoscope system according to claim 5, wherein said light having the special wavelength is UV light.

14. The electronic endoscope system according to claim 5, said first illuminating unit including a white light source that emits white light, said second illuminating unit including a second light source that emits light having a special wavelength, said electronic endoscope further comprising a controller that controls said second light source to turn ON and OFF, wherein if said second light source is turned OFF and said at least one switch is held in an operative position for a predetermined duration of time, said second light source is turned ON, and wherein if said second light source is turned ON and said at least one switch is held in an operative position for a predetermined duration of time, said second light source is turned OFF.

15. The electronic endoscope system according to claim 14, said at least one switch including a foot switch which is operable by a foot of the operator.

16. The electronic endoscope system according to claim 14, said scope unit being provided with an instrument channel through which a treatment tool is insertable, said at least one switch including a manually operable switch arranged adjacent to an inlet of said instrument channel.

17. The electronic endoscope system according to claim 14, said scope unit having an operation portion, at which operation switches are provided, said at least one switch including another manually operable switch arranged at said operation portion.

* * * * *